(12) United States Patent
Okombi et al.

(10) Patent No.: US 9,089,499 B2
(45) Date of Patent: *Jul. 28, 2015

(54) PARA-COUMARIC ACID OR PARA-HYDROXYCINNAMIC ACID DERIVATIVES AND THEIR USE IN COSMETIC OR DERMATOLOGICAL COMPOSITIONS

(71) Applicants: BASF Beauty Care Solutions France S.A.S., Lyons (FR); Universite Joseph Fourier-Grenoble 1., Grenoble (FR)

(72) Inventors: Sabrina Okombi, Grenoble (FR); Delphine Rival, Ternay (FR); Ahcene Boumendjel, Meylan (FR); Anne-Marie Mariotte, Saint Simeon de Bressieux (FR); Eric Perrier, Les Cotes D'arey (FR)

(73) Assignees: Universite Joseph Fourier-Grenoble 1, Grenoble (FR); BASF Beauty Care Solutions France S.A.S., Lyons (FR)

( * ) Notice: Subject to any disclaimer, the term of this patent is extended or adjusted under 35 U.S.C. 154(b) by 113 days.

This patent is subject to a terminal disclaimer.

(21) Appl. No.: 13/913,896

(22) Filed: Jun. 10, 2013

(65) Prior Publication Data
US 2013/0272983 A1 Oct. 17, 2013

Related U.S. Application Data

(63) Continuation of application No. 13/152,718, filed on Jun. 3, 2011, now Pat. No. 8,481,593, which is a continuation of application No. 11/594,440, filed on Nov. 8, 2006, now abandoned.

(30) Foreign Application Priority Data

Nov. 8, 2005 (FR) .................................. 05 11364

(51) Int. Cl.
| | | |
|---|---|---|
| *A61K 8/37* | (2006.01) | |
| *A61K 8/42* | (2006.01) | |
| *A61K 8/55* | (2006.01) | |
| *A61Q 17/00* | (2006.01) | |
| *A61Q 19/00* | (2006.01) | |
| *A61Q 1/06* | (2006.01) | |
| *A61Q 5/02* | (2006.01) | |
| *A61Q 19/02* | (2006.01) | |
| *A61K 8/46* | (2006.01) | |

(Continued)

(52) U.S. Cl.
CPC ... *A61K 8/55* (2013.01); *A61K 8/37* (2013.01); *A61K 8/375* (2013.01); *A61K 8/42* (2013.01); *A61K 8/463* (2013.01); *A61Q 19/00* (2013.01); *A61Q 19/02* (2013.01); *A61K 2800/782* (2013.01); *A61Q 1/06* (2013.01); *A61Q 1/10* (2013.01); *A61Q 5/02* (2013.01); *A61Q 17/00* (2013.01); *A61Q 19/10* (2013.01)

(58) Field of Classification Search
CPC .......... G06F 8/66; G06F 9/268; G06F 9/328; A61K 2800/782; A61K 8/37; A61K 8/375; A61K 8/42; A61K 8/463; A61K 8/55; A61Q 17/00; A61Q 19/00; A61Q 19/02; A61Q 19/10; A61Q 1/06; A61Q 1/10; A61Q 5/02
USPC ........................................................ 424/62
See application file for complete search history.

(56) References Cited

U.S. PATENT DOCUMENTS

| 4,978,523 A | 12/1990 | Motegi et al. | |
|---|---|---|---|
| 5,164,185 A | 11/1992 | Charpin et al. | ............... 424/401 |
| 5,610,185 A | 3/1997 | Stanwell et al. | ............... 514/544 |

(Continued)

FOREIGN PATENT DOCUMENTS

| EP | 0 900 781 A | 3/1999 | ............ C07C 235/34 |
|---|---|---|---|
| EP | 1 430 883 A | 6/2004 | ............... A61K 7/48 |

(Continued)

OTHER PUBLICATIONS

Ley International Journal of Cosmetic Science 2001, 23, 35-48.*

(Continued)

*Primary Examiner* — Ernst V Arnold
(74) *Attorney, Agent, or Firm* — Drinker Biddle & Reath LLP

(57) ABSTRACT

The invention relates to the use of para-coumaric acid or para-hydroxycinnamic acid derivatives in cosmetic or dermatological compositions, specifically to the use of at least one compound derived from para-coumaric acid having a general formula (I) below:

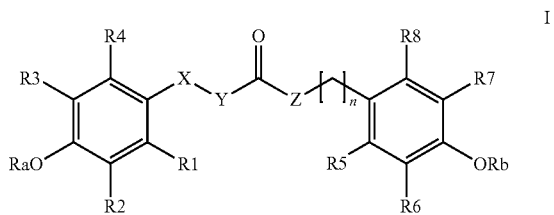

in which, especially, Z represents an oxygen or an —NH— group; X and Y are identical and each represent a CH or $CH_2$ group, as an active principle with depigmenting, free-radical-scavenging and/or antiinflammatory activity. The invention also relates to the use of the above compounds for cosmetic care or for the preparation of a pharmaceutical composition, especially for depigmenting an area of skin, having antiradical and/or antiinflammatory activity.

25 Claims, No Drawings

(51) Int. Cl.
*A61Q 1/10* (2006.01)
*A61Q 19/10* (2006.01)

(56) References Cited

U.S. PATENT DOCUMENTS

| | | | |
|---|---|---|---|
| 5,719,129 A | 2/1998 | Andary et al. | 514/25 |
| 5,773,014 A | 6/1998 | Perrier et al. | 424/401 |
| 6,117,365 A | 9/2000 | Ley | 252/401 |
| 2003/0152682 A1 | 8/2003 | Ley et al. | |
| 2003/0162789 A1 | 8/2003 | Park et al. | 514/252.13 |
| 2004/0185023 A1 | 9/2004 | Schnittger et al. | |
| 2007/0292493 A1 | 12/2007 | Brierre | |

FOREIGN PATENT DOCUMENTS

| | | | |
|---|---|---|---|
| JP | 57-146583 A | 9/1982 | |
| JP | 59-196813 | 8/1984 | |
| JP | 11-228514 | 8/1999 | |
| JP | 2000129257 A | 5/2000 | |
| KR | 2005/0091116 A | 9/2005 | |
| WO | WO 99/22728 | 5/1999 | A61K 31/35 |
| WO | WO-01/07004 A1 | 2/2001 | |
| WO | 03101927 A1 | 12/2003 | |
| WO | WO 2004/002941 A1 | 1/2004 | C07C 233/18 |

OTHER PUBLICATIONS

ATCC "Formulation for Dulbecco's Modified Eagle's Medium (DMEM) ATCC 30-220", www.atcc.org/attachments/4890.pdf, Aug. 12, 2012.
Lee, et al., "Cytotoxicity of phenolic acid phenethyl esters on oral cancer cells", Cancer Letters 223 (2005): 19-25.
Okombi, et al. "Analogues of N-hydroxycinnamoylphenalkylamides as inhibitors of human melanocyte-tyrosinase", Bioorganic & Medicinal Chemistry Letters 16 (2006): 2252-2255.
Hirang, H. et al., "Isolation of Free Radical Scavenger from Coptidis Rhizoma", *Natural Medicines*, vol. 51, No. 6, (1997), pp. 539-540.
Tseng, C.-F., et al, Inhibition of In Vitro Prostaglandin and Leukotriene Biosyntheses by Cinnamoyl-beta-phenethylamine and N-Acyldopamine Derivatives, Chem. Pharm. Bull vol. 40, No. 2, (1992) pp. 398-400.
British Intellectual Property Office Search Report, dated Oct. 28, 2009.
F. Darwish et al., "Ecdysteroids and other constiuents from *Sida spinosa* L.", Phytochemistry, vol. 62, 2003, pp. 1179-1184, see especially compound (5) on p. 1181,[vs. claim 1 at least].
A. El-Moussallamy et al., "Teuorol, a decarboxyrosmarinic acid and Its 4'-O-triglycoside, teuoroside from Teucrium pilosum", Phytochemistry, vol. 55, 2000, pp. 927-931, see especially 1 on page 928, [vs claim 1 at least].
Search Report from United Kingdom for Application No. GB0622038.8 dated Mar. 1, 2007.
Patent Abstracts of Japan for Application No. 10343539 filed Nov. 27, 1998.
Patent Abstracts of Japan for Application No. 2005004942 filed Jan. 12, 2005.
Tada et al., "Synthetic Search for Cosmetic Ingredients; Preparations, Tyrosinase Inhibitory and Antioxidant Activities of Caffeic Amides" *J. Oleo Sci.*, 2002, vol. 51, No. 1, pp. 19-27.
Roh et al., "Inhibitory Effects of Active Compounds Isolated from Safflower (*Carthamus tinctorius* L.) Seeds for Melanogenesis" *Biol. Pharm. Bull.*, 2004, vol. 27, No. 12, pp. 1976-1978.
Search Report from France for Application No. FR0511364, dated Sep. 29, 2006.
International Journal of Cosmetic Science 23 (1), 35-48 CODEN: IJCMDW; ISSN: 0142-5463, 2001, XP002398893.
Masaki, H., et al., "A new approach for development of whitening agents—A role of active oxygen species on melanogenesis", Fragrance Journal, vol. 28, No. 9, (2000), pp. 16-23.
Kim, Y., et al., "Inhibitory Phenolic Amides on Lipopolysaccharide-induced Nitric Oxide Production in RAW 264.7 cells from *Beta vulgaris* var. *cicla* Seeds", Phytotherapy Research, vol. 17, (2003), pp. 983-985.

\* cited by examiner

PARA-COUMARIC ACID OR PARA-HYDROXYCINNAMIC ACID DERIVATIVES AND THEIR USE IN COSMETIC OR DERMATOLOGICAL COMPOSITIONS

RELATED APPLICATIONS

This application is a continuation of U.S. application Ser. No. 13/152,718, filed Jun. 3, 2011, which is a continuation of U.S. application Ser. No. 11/594,440, filed Nov. 8, 2006, which claims priority from French patent application serial number 0511364, filed Nov. 8, 2005, the entire contents of each of which are hereby incorporated by reference in this application.

FIELD OF THE INVENTION

The present invention relates essentially to the use of at least one para-coumaric (also referred to as "p-coumaric") acid derivative as an active agent for the manufacture of a cosmetic or pharmaceutical, and especially a dermatological or topical composition, with depigmenting activity or with an inhibitory effect on melanogenesis, and/or with antiradical and/or antiinflammatory activity.

The invention also covers cosmetic compositions or pharmaceutical and especially dermatological compositions, thus obtained, with depigmenting activity or with an inhibitory effect on melanogenesis, and/or with antiradical and/or antiinflammatory activity.

The invention also covers a cosmetic care process or a therapeutic depigmentation treatment process using p-coumaric acid derivatives as depigmenting active agents.

The invention also covers a cosmetic care process or a therapeutic treatment process for obtaining an antiradical and/or antiinflammatory effect using the abovementioned p-coumaric acid derivatives.

BACKGROUND OF THE INVENTION

To combat solar radiation, the skin has differentiated cells that are particularly suited to this function: the melanocytes. In the course of a complex process, melanogenesis, these cells manufacture melanin, a dark pigment which has the effect of protecting the skin structures and of increasing the time required to contract a solar erythema. However, not all melanins are protective. In particular, there exists one form of melanin, known as phaeomelanin, that is extremely phototoxic. Like all melanins, it is capable of reacting with certain forms of free radicals, but it can also cause the formation of free radicals that are even more toxic, and which are liable to cause irreversible damage to the genetic material of keratinocytes. Moreover, certain disorders associated with dysfunction of the melanization unit are liable to cause hyperpigmentation, which is occasionally particularly unsightly.

Thus, the use of melanin synthesis inhibitors is particularly advantageous in cosmetology, not only for applications in which true depigmentation is desired, as in the case of the bleaching of highly pigmented skin or the inhibition of hyperpigmentation in certain unaesthetic aspects, for example, but also for applications for lightening the complexion and for giving luminosity to the skin and radiance to the surface tissues. This inhibition of melanin synthesis may also be particularly advantageous in the context of therapeutic treatment for treating a true pathology.

para-Coumaric or para-hydroxycinnamic acids have been described as inhibitors of melanin production in numerous studies. However, these substances do not make it possible to obtain significant inhibitory effects on melanin synthesis. This excessively weak activity does not make it possible to obtain strong enough effects and these substances are thus little used in cosmetic or pharmaceutical topical applications for effectively combating unsightly pigmentations.

The prior art mentions in particular the use of vitamin C (or derivatives thereof) or kojic acid (or derivatives thereof) for inhibiting tyrosinase, but these molecules are either cytotoxic at the concentration used, or of little efficacy. It is known practice in particular to use ferulic acid or caffeic acid as depigmenting agent in cosmetic compositions. However, these compositions are not entirely satisfactory as regards the efficacy of the depigmenting action.

Thus, an aim of the present invention is essentially to solve the technical problem that consists in providing a depigmenting agent that is more active than those currently used, such as caffeic acid or ferulic acid.

Another aim of the present invention is also to provide compositions using these depigmenting agents, cosmetic care methods and/or pharmaceutical treatment methods using these depigmenting agents, and also the use of these depigmenting agents to exert antiradical and/or antiinflammatory activity.

A further aim of the present invention is also to provide compositions whose active compounds are extracted from plants.

Yet a further aim of the present invention is also to provide compositions that can be applied topically.

An additional aim of the present invention is also to provide depigmenting agents for combating skin hyperpigmentation, especially for aesthetic purposes, mainly when the skin has at least one hyperpigmented localized area.

A further aim of the present invention is to solve the technical problems mentioned above in a safe and reliable way and especially while avoiding undesirable side effects, particularly in human beings, for example by reducing the cytotoxicity of the active agents used.

SUMMARY OF THE INVENTION

The present invention solves the problems mentioned above through the synthesis of novel chemical derivatives of para-coumaric acid, in particular of caffeic acid, ferulic acid, or even hybrid derivatives of these two molecules in certain cases. The inhibitory effect on melanin synthesis of these novel derivative molecules thus described is extremely strong, the toxicological profile of these molecules is perfect for cosmetic and dermopharmaceutical applications, and the incorporation of these substances into cosmetic or pharmaceutical formulations is possible without any major problems being encountered. These substances are thus entirely suitable in the context of cosmetic and pharmaceutical applications.

Moreover, by comparing the depigmenting effect of the substances obtained in accordance with the present invention, which in one preferred embodiment are para-coumaric acid derivatives grafted onto tyramine, dopamine or tyrosol derivatives, with the effect of compounds derived from para-coumaric acid, such as caffeic acid or ferulic acid as a mixture with tyramine, dopamine or tyrosol, it was unexpectedly found that the activity of the compounds of the present invention is markedly superior with reference to said mixture.

Thus, the present invention relates to the use of an effective amount of at least one compound derived from para-coumaric acid of general formula (I) below:

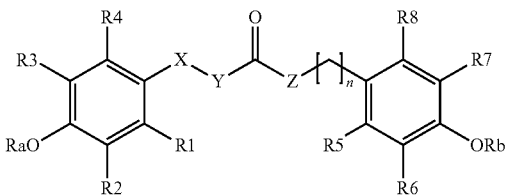

in which:
Z represents an oxygen or an —NH— group;
X and Y are identical and each represent a CH group (cis or trans) or $CH_2$ group;
n is a number, preferably an integer, ranging from 1 to 12;
Ra and Rb are identical or different, preferably identical, and represent a hydrogen atom, a linear or branched acyl group, preferably of C1-12, a linear or branched, saturated or unsaturated alkyl group, preferably of C1-12; a salified or non-salified sulfonyl group ($SO_3H$); or a salified or non-salified phosphonate group ($PO_3H_2$); ORa and/or ORb possibly being in the presence of a base in dissociated form, for example in a form O—Na+;
$R_1$, $R_2$, $R_3$, $R_4$, $R_5$, $R_6$, $R_7$ and $R_8$ represent, independently of each other: a hydrogen atom; a hydroxyl group; a halogen atom; a salified or non-salified acid function; an aldehyde function; an amide function; an amine function (primary, secondary or tertiary) in basic or salified form; a cyano group; a thiol group; a nitro group; a sugar (O-heteroside); a linear or branched alkoxide group, preferably of C1-12; a linear or branched alkyl chain, preferably of C1-12; a linear or branched alkenyl chain, preferably of C1-12; a linear or branched thioalkyl chain, preferably of C1-12; a linear or branched alkoxy chain, preferably of C1-12; an alkenyloxy chain, preferably of C1-12; a salified or non-salified sulfate group; a salified or non-salified sulfonyl group; a salified or non-salified phosphonate group; a salified or non-salified phosphate group; a silanol group; in which the carbon-based chains, preferably of C1-C12, may be substituted;

as active principle in a cosmetic or pharmaceutical composition. In a particularly preferred embodiment, the composition is applied topically. The term "effective amount" as used herein means an amount of the compound or composition sufficient to significantly induce a positive benefit, including independently or in combinations the benefits disclosed herein.

Advantageously, the compounds used are the trans compounds, although the invention also covers the cis compounds or a cis/trans mixture, which preferably comprises a larger amount of trans compounds.

DETAILED DESCRIPTION OF THE INVENTION

In the text hereinbelow, the groups identified generally (Ra, Rb, R1, R2, etc.) refer to any formula comprising the said groups, and especially to the general formula I. Thus, all combinations that may be made from the advantageous embodiments are to covered by the present invention.

Advantageously, the present invention covers the use of an effective amount of at least one compound derived from para-coumaric acid having the general formula (I) as defined above, as a depigmenting agent, or as an active principle with antiradical or antiinflammatory activity, in a topical composition. Such topical composition generally further include a dermatologically acceptable carrier. The term "dermatologically acceptable" as used herein, means that the compositions or components thereof, are suitable for use in contact with human skin tissue without undue toxicity, incompatibility, instability, allergic response, and the like. Such carriers may be approved as acceptable for cosmetic uses, pharmaceutical uses, or both, depending upon the intended uses of the topical composition being formulated.

Advantageously, Ra and Rb each independently represent a hydrogen atom, a linear or branched C1-12 acyl group, a salified or non-salified sulfonyl group ($SO_3H$); a salified or non-salified phosphonate group ($PO_3H_2$), and preferably a hydrogen atom.

Advantageously, preferred derivatives are represented by the chemical formula II, in which the groups $R_1$ to $R_8$, X, Y, Z and n represent the elements cited in the formula I:

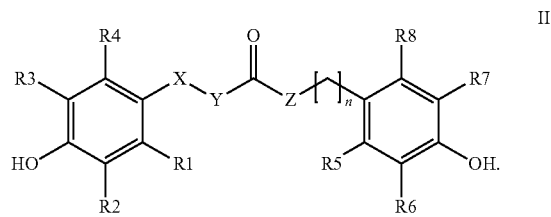

Advantageously, preferred derivatives are represented by the chemical formula III, in which the groups $R_2$, $R_3$, $R_6$ and $R_7$, X, Y, Z and n represent the elements cited in the general formula I:

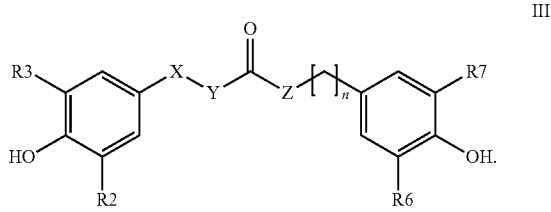

Preferably, the invention covers para-coumaric acid derivatives, known as ferulic acid derivatives, corresponding to the general formula I in which:

Ra, Rb, $R_1$, $R_4$, $R_5$ and $R_8$ preferentially represent a hydrogen,
$R_3$ preferentially represents a methoxy group, and $R_2$ is a hydrogen,
X and Y each represent a CH group and n is equal to 2, These derivatives may be represented by the following formulae (IVa and IVb) in which $R_6$ and $R_7$ represent the elements cited in the general formula I:

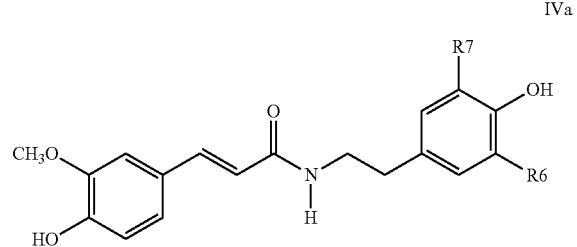

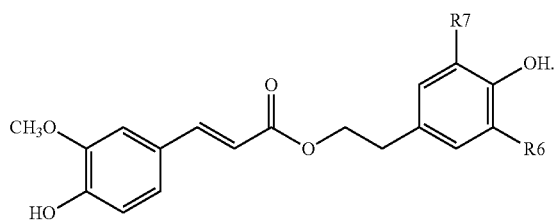

In the above formulae IVa and IVb, $R_6$ and $R_7$ are preferentially hydrogens, which corresponds to the derivatives described by formulae IVa1 and IVb1 below:

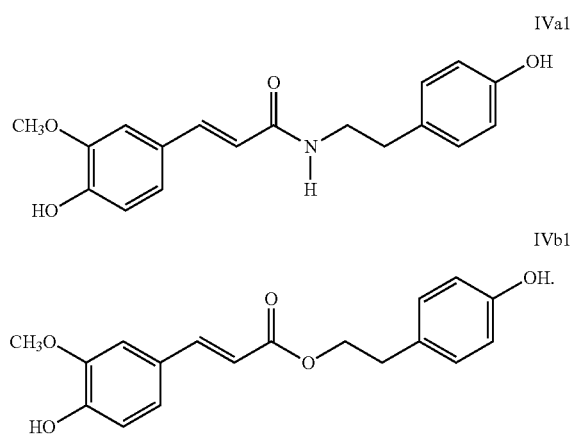

Preferably, the compounds also concerned in this invention are the para-coumaric acid derivatives known as caffeic acid derivatives, corresponding to the general formula I in which: Ra and Rb, $R_1$, $R_2$, $R_4$, $R_5$ and $R_8$ preferentially represent a hydrogen, $R_3$ preferentially represents a hydroxyl, and $R_2$ is a hydrogen, X and Y each represent a CH and n is equal to 2. These derivatives are represented by the following formulae (Va and Vb) in which $R_6$ and $R_7$ represent the elements cited in the general formula I:

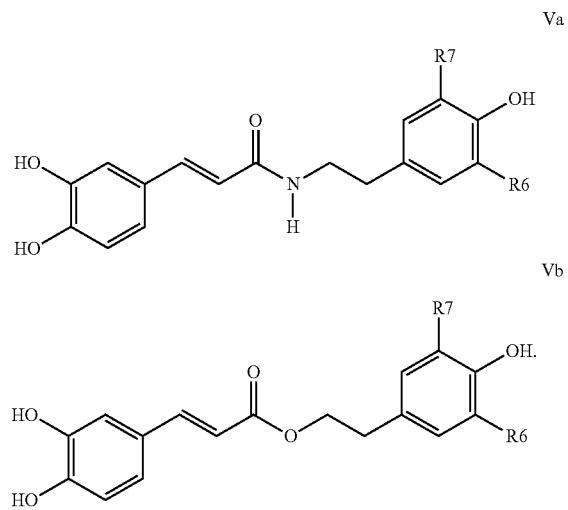

In formulae Va and Vb, $R_6$ and $R_7$ are preferentially hydrogens, which corresponds to the two derivatives described by formulae Va1 and Vb1 below:

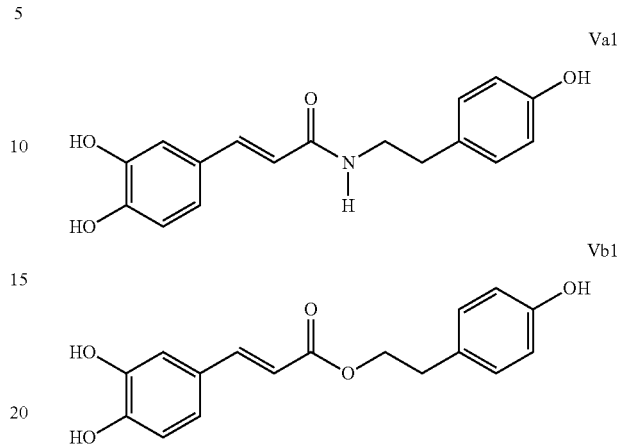

The invention also relates to the para-coumaric acid derivatives corresponding to the general formula I in which the substituents Ra, Rb, $R_1$, $R_2$, $R_3$, $R_4$, $R_5$, $R_6$, $R_7$ and $R_8$ represent a hydrogen and n is preferentially equal to 2. Advantageously, $R_1$, $R_4$, $R_5$, and $R_8$ represent a hydrogen. Advantageously, the substituents $R_2$ and $R_3$ are chosen from a hydroxyl group, optionally in salified form, or methoxy, and a hydrogen atom. Advantageously, the substituents $R_6$ and $R_7$ are chosen from a hydroxyl group, optionally in salified form, or methoxy, and a hydrogen atom. Preferably, n=2. Advantageously, the substituents $R_6$ and $R_7$ are chosen from a hydroxyl group, optionally in salified form, and a hydrogen atom.

According to a first embodiment, the para-coumaric acid derivatives are ferulic acid derivatives in which Ra, Rb, $R_1$, $R_2$ and $R_4$ preferentially represent a hydrogen atom; $R_3$ preferentially represents a methoxy group; X and Y each represent a CH group and n is equal to 2; these derivatives possibly being represented by the following to formulae (IIa and IIb):

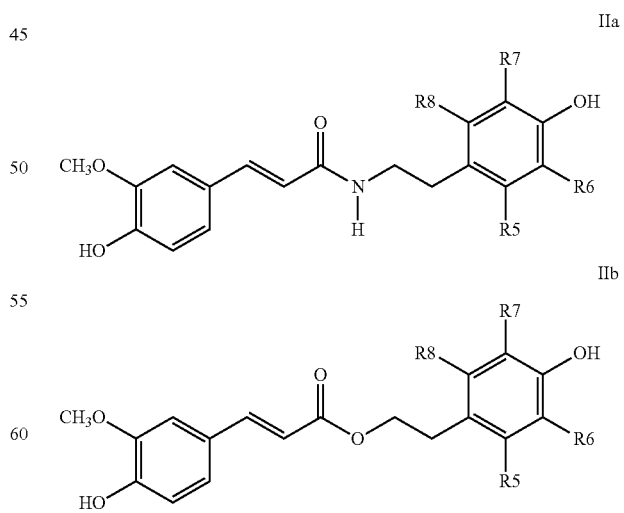

in which $R_5$, $R_6$, $R_7$ and $R_8$ are as defined above. Advantageously, in formulae IIa and IIb, $R_5$, $R_6$, $R_7$ and $R_8$ each represent a hydrogen atom.

According to a second embodiment, in formulae IIa and IIb, $R_5$, $R_6$ and $R_8$ each represent a hydrogen atom and $R_7$ represents a hydroxyl group, which corresponds to the two derivatives described by the following formulae:

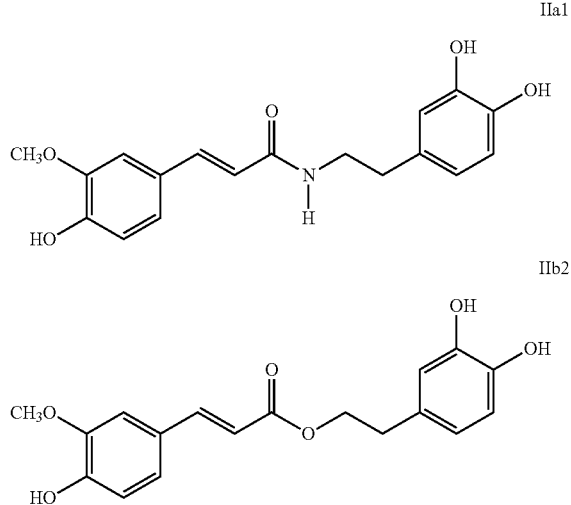

Advantageously, the para-coumaric acid derivatives are caffeic acid derivatives in which Ra, Rb, $R_1$, $R_2$ and $R_4$ preferentially represent a hydrogen atom; $R_3$ preferentially represents a hydroxyl group; X and Y each represent a CH group and n is equal to 2; these derivatives possibly being represented by the following formulae (IIIa and IIIb):

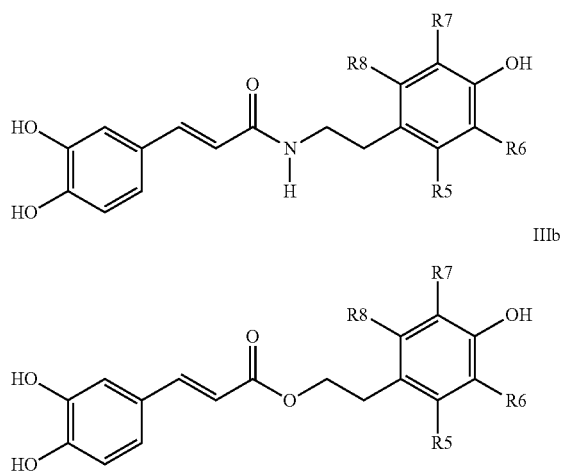

in which:

$R_5$, $R_6$, $R_7$ and $R_8$ are as defined above.

Advantageously, in formulae IIIc and IIIb, $R_5$, $R_6$, $R_7$ and $R_8$ each represent a hydrogen atom. Advantageously, in formulae IIIc and IIIb, $R_5$, $R_6$, $R_8$ each represent a hydrogen atom and $R_7$ represents a hydroxyl group, which corresponds to the two derivatives described by formulae IIIa1 and IIIb2 below:

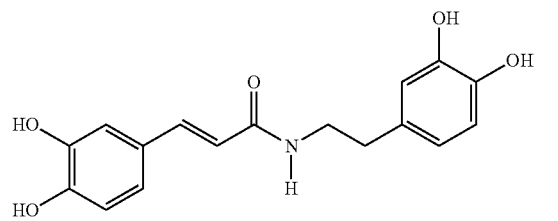

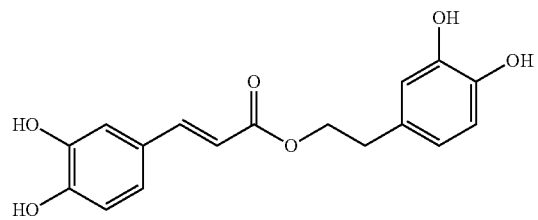

Advantageously, the substituents Ra, Rb, $R_1$, $R_2$, $R_4$, $R_5$, $R_6$, $R_7$ and $R_8$ each represent a hydrogen atom, $R_3$ represents a hydroxyl group, n is equal to 2, these derivatives possibly being represented by the following formulae (VIa and VIb) in which X and Y are CH or $CH_2$ groups:

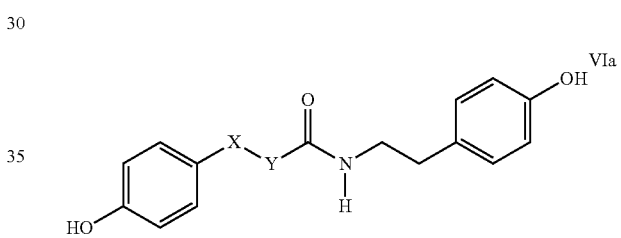

According to one advantageous embodiment, the compound is extracted from a plant, said extract preferably comprising a compound chosen from:

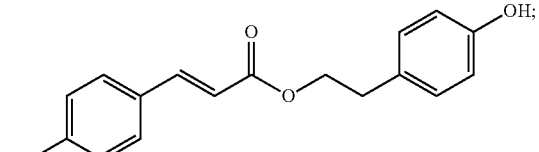

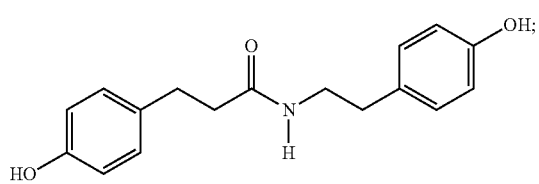

-continued

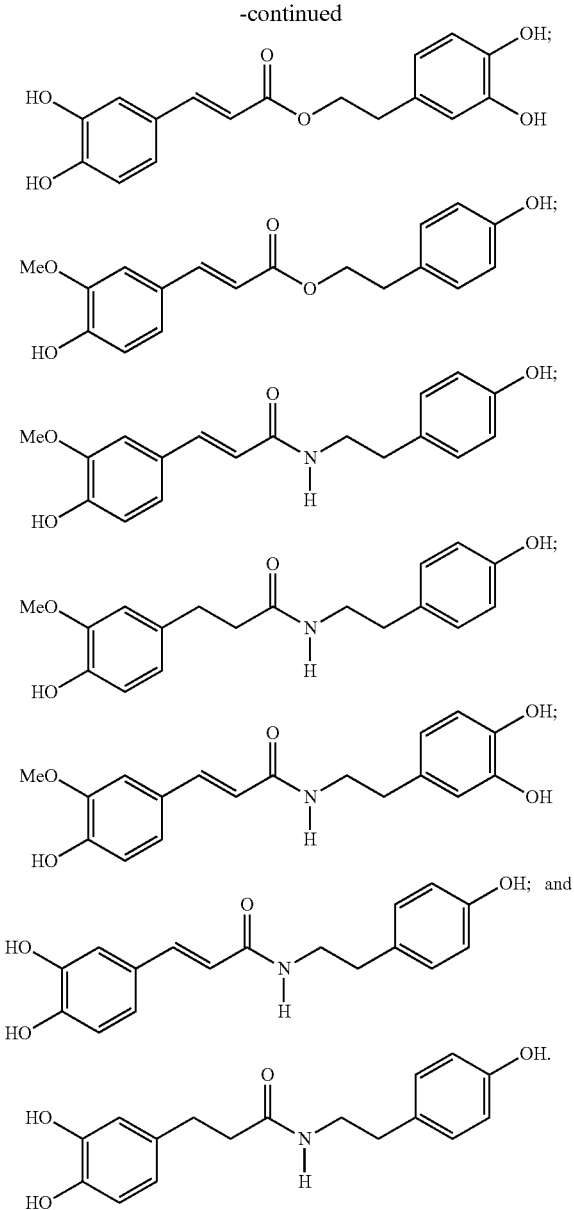

It is entirely advantageous to use, in particular in cosmetics, natural compounds, in particular derived from plants, so as to provide users with a guarantee of the healthy origin of the active compounds used. A person skilled in the art also knows the various advantages of using natural compounds extracted from plants.

It is advantageous to obtain an extract of plants used as raw material using a solvent, preferably a polar solvent, and preferably water, a water/alcohol mixture or polyol, for instance a water/glycol or water/ethanol mixture, or a polyol, or an alcohol, for instance ethanol. Ethyl acetate or acetone, or any mixture of the solvents mentioned above, may also be used. The extract is preferably filtered and then dried. It is also possible to perform the extraction with moderate heating, for instance to 45° C. The extraction is preferably performed with stirring. The extraction processes are well known to those skilled in the art. The part of the plants used may vary as a function of the extract to be obtained.

The invention relates in particular to the use of the compounds mentioned above for exerting depigmenting activity or an inhibitory effect on melanogenesis, especially via topical application to at least one area of skin tissue of an individual.

The invention relates in particular to the use of the compounds mentioned above for reducing the pigmentation of the said area of skin tissue.

The invention also relates to a cosmetic care process, comprising the topical application of a composition as defined above. The term "topical application", as used herein, means to apply or spread the compositions of the present invention onto the surface of skin tissue. Such cosmetic care processes include methods of Advantageously, the cosmetic care makes it possible to reduce the pigmentation of the skin in the area of application.

The invention also relates to the formulation of topically applied cosmetic compositions comprising the para-coumaric derivative compounds described herein. These cosmetic compositions generally further comAdditionally, as a large number of cosmetic active ingredients are known in the art to improve the health and/or physical appearance of the skin, the skilled artisan will also recognize that it is useful to formulate cosmetic compositions capable of providing multiple benefits to the skin of an individual, and further, that the compounds described herein may have a synergistic effect when combined with one or more additional cosmetic active ingredients. Thus, cosmetic compositions comprising the compounds described herein may further comprise additional cosmetic active ingredients. Preferably, as the composition is to be in contact with human skin tissue, the additional components should be suitable for application to such tissue, that is, when incorporated into the composition they are suitable for use in contact with human skin tissue without undue toxicity, incompatibility, instability, allergic response, and the like within the scope of sound medical judgment. The CTFA Cosmetic Ingredient Handbook, Second Edition (1992) describes a wide variety of non-limiting cosmetic and pharmaceutical ingredients commonly used in the skin care industry, which are suitable for use in the topical compositions of the present invention. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

The invention also relates to the use of an effective amount of at least one compound as defined above for the preparation of a pharmaceutical composition for exerting depigmenting activity or an inhibitory effect on melanogenesis, especially via topical application to at least one area of skin tissue of an individual with hyperpigmentation.

The invention also relates to the use of an effective amount of at least one compound as defined above for the preparation of a cosmetic or pharmaceutical composition for exerting antiradical and/or antiinflammatory activity. Specifically, by virtue of their antiradical activity, the compounds derived from the invention can reduce the L-dopa molecule so as to stop its oxidation into chromophoric compound. By virtue of their high antiradical activity, the compounds derived from the invention are antiinflammatory compounds: specifically, the free radicals generated during a UV stress or the like induce the inflammation cascade. This is why compounds with antiradical properties inhibit the inflammation cascade.

The invention relates in particular to the following preferred compounds, which are particularly illustrated.

However, other aims, characteristics and advantages of the invention will emerge clearly to a person skilled in the art after reading the explanatory description that refers to the examples, which are given purely as illustrations and should not be considered as limiting the scope of the invention in any way.

The examples form an integral part of the present invention and any characteristic appearing novel relative to any prior art from the description taken in its entirety, including the examples, forms an integral part of the invention in its function and in its generality. Thus, each example has a general scope.

Moreover, in the examples, all the percentages are given on a weight basis, unless otherwise indicated, and the temperature is expressed in degrees Celsius unless otherwise indicated, and the pressure is atmospheric pressure, unless otherwise indicated.

EXAMPLES

I—Ferulic acid (4-hydroxy-3-methoxycinnamic acid) derivatives

Example 1

N-trans-feruloyldopamine(SO-I-146)

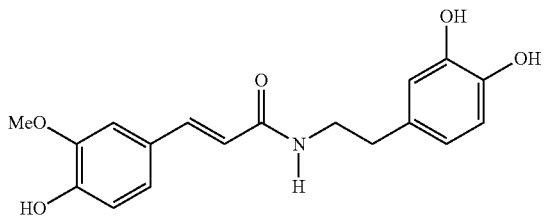 [SMILES: COc1cc(/C=C/C(=O)NCCc2ccc(O)c(O)c2)ccc1O]

A solution of ferulic acid (300 mg; 1.54 mmol) and of triethylamine (1.5 eq; 2.31 mmol) in DMF (3.5 mL) is cooled to 3 or 4° C. using an ice bath. An amine, 3-hydroxytyramine (dopamine) (1 eq; 1.54 mmol) is added to the medium, followed by addition of a solution of BOP (benzotriazol-1-yloxy)tris(dimethylamino)phosphonium hexafluorophosphate; (1 eq; 1.54 mmol) in dichloromethane (3.5 mL); the mixture is stirred for about thirty minutes in the ice bath and then for 20 hours at room temperature. Stirring is then stopped and the dichloromethane is evaporated off under vacuum. 30 mL of water are added to the remaining solution and the mixture obtained is extracted with ethyl acetate (3×75 mL). The organic phase is successively washed with 100 mL of 1N HCl solution, 100 mL of water and 100 mL of 1M sodium bicarbonate (NaHCO$_3$) solution. It is then dried over sodium sulfate and evaporated to dryness. The product obtained is in the form of a white precipitate after chromatography on a column of silica gel.

Example 2

N-trans-feruloyl-3,4-dimethoxydopamine

The protocol derived from Example 1 is applied with ferulic acid and 2-(3,4-dimethoxyphenyl)ethylamine instead of ferulic acid and dopamine; the compound obtained is N-trans-feruloyl-3,4-dimethoxydopamine.

Example 3

N-trans-feruloyltyramine

The protocol derived from Example 1 is applied with ferulic acid and tyramine instead of ferulic acid and dopamine; the compound obtained is N-trans-feruloyltyramine.

Example 4

N-trans-feruloyl-4-hydroxy-3-methoxyphenylmethylamine

The protocol derived from Example 1 is applied with ferulic acid and 4-hydroxy-3-methoxybenzylamine instead of ferulic acid and dopamine; the compound obtained is N-trans-feruloyl-4-hydroxy-3-methoxyphenylmethylamine.

Example 5

N-dihydroferuloyltyramine

The protocol derived from Example 1 is applied with dihydroferulic acid and tyramine instead of ferulic acid and dopamine; the compound obtained is N-dihydroferuloyltyramine.

Example 6

N-dihydroferuloyldopamine

The protocol derived from Example 1 is applied with dihydroferulic acid and 3-hydroxytyramine instead of ferulic acid and dopamine; the compound obtained is N-dihydroferuloyldopamine.

Example 7

Synthesis of a ferulic acid ester: 2-(p-hydroxyphenylethyl)trans-ferulate

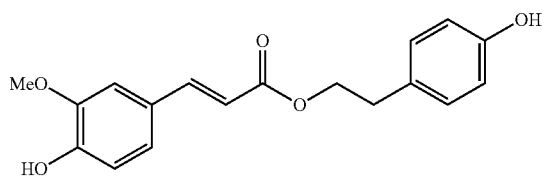 [SMILES: COc1cc(/C=C/C(=O)OCCc2ccc(O)cc2)ccc1O]

Ferulic acid (4-hydroxy-3-methoxycinnamic acid, 250 mg, 1.28 mmol) is dissolved in dichloromethane (10 mL) and DMAP (dimethylaminopyridine, 157 mg; 1.28 mmol) is added. After dissolving the two products, tyrosol (353.7 mg; 2.56 mmol) is added, followed by addition of EDCI [1-(3- dimethylaminopropyl)-3-ethylcarbodiimide; 368 mg; 1.92 mmol]. The mixture obtained is stirred for 20 hours at room temperature. The reaction medium is then diluted with ethyl acetate (32 mL) and water (6 mL). The organic phase is separated from the aqueous phase, which is re-extracted with ethyl acetate. The organic phases are combined, dried over magnesium sulfate, washed with saturated NaCl solution and evaporated to dryness. The product is obtained in the form of a white precipitate after chromatography on a column of silica gel, using a 5/5 ethyl acetate/cyclohexane mixture.

Example 8

2-(3,4-dihydroxyphenylethyl)trans-ferulate

The protocol derived from Example 7 above is applied with ferulic acid and 3-hydroxytyrosol instead of ferulic acid and tyrosol; the compound obtained is 3,4-dihydroxyphenylethyl trans-ferulate (formula IVb2)

II—Caffeic acid (3,4-dihydroxycinnamic acid) derivatives

Example 9

N-trans-caffeoyltyramine

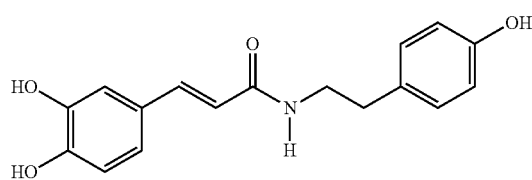 [SMILES: O=C(/C=C/c1ccc(O)c(O)c1)NCCc1ccc(O)cc1]

A solution of caffeic acid (300 mg; 1.66 mmol) and of triethylamine (1.5 eq; 2.49 mmol) in DMF (3.5 mL) is cooled to 4° C. using an ice bath. An amine, tyramine (1 eq; 1.66 mmol) is added to the medium, followed by addition of a solution of BOP (benzotriazol-1-yloxy)tris(dimethylamino) phosphonium hexafluorophosphate; 1 eq; 1.66 mmol) in dichloromethane (3.5 mL); the mixture is stirred for about thirty minutes in the ice bath and then for 20 hours at room temperature. Stirring is then stopped and the dichloromethane is evaporated off under vacuum. 30 mL of water are added to the remaining solution and the mixture obtained is extracted with ethyl acetate (3×75 mL). The organic phase is successively washed with 100 mL of 1N HCl solution, 100 mL of water and 100 mL of 1M sodium bicarbonate ($NaHCO_3$) solution. It is then dried over sodium sulfate and evaporated to dryness. The product is obtained in the form of a white precipitate after purification by chromatography on a column of silica gel.

Example 10

N-trans-caffeoyldopamine

The protocol derived from Example 9 is applied with caffeic acid and 3-hydroxytyramine (dopamine) instead of caffeic acid and tyramine; the compound obtained is N-trans-caffeoyldopamine.

Example 11

N-trans-caffeoyl-4-hydroxy-3-methoxyphenylmethylamine

The protocol derived from Example 9 is applied with caffeic acid and 4-hydroxy-3-methoxybenzylamine instead of caffeic acid and tyramine; the compound obtained is N-trans-caffeoyl-4-hydroxy-3-methoxyphenyl methylamine.

Example 12

N-trans-caffeoyl-3,4-dimethoxydopamine

The protocol derived from Example 9 is applied with caffeic acid and 2-(3,4-dimethoxyphenyl)ethylamine instead of caffeic acid and tyramine; the compound obtained is N-trans-caffeoyl-3,4-dimethoxydopamine.

Example 13 dihydrocaffeoyltyramine

The protocol derived from Example 9 is applied with 3-(3, 4-dihydroxyphenyl)propionic acid and tyramine instead of caffeic acid and tyramine; the compound obtained is dihydrocaffeoyltyramine.

Example 14

Synthesis of a caffeic acid ester:
2-(4-hydroxyphenyl)ethyl trans-caffeoate (formula IVb1)

The protocol derived from Example 7 is applied with caffeic acid and tyrosol instead of ferulic acid and tyrosol; the compound obtained is 2-(4-hydroxyphenylethyl) trans-caffeoate (formula IVb1).

Example 15

2-(3,4-dihydroxyphenyl)ethyl trans-caffeoate (formula IVb2)

The protocol derived from Example 14 above is applied with caffeic acid and 3-hydroxytyrosol instead of caffeic acid and tyrosol; the compound obtained is 2-(3,4-dihydroxyphenylethyl)trans-caffeoate (formula IVb2).

III—COUMARIC ACID 4-hdroxycinnamic acid) DERIVATIVES

Example 16

N-dihydrocoumaroyltyramine

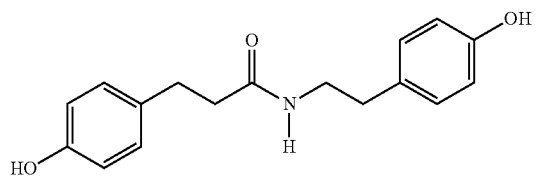 [SMILES: O=C(CCc1ccc(O)cc1)NCCc1ccc(O)cc1]

A solution of 3-(4-hydroxyphenyl)propionic acid or p-dihydrocoumaric acid (1 g; 6.02 mmol) and of triethylamine (1.5 eq; 9.03 mmol) in DMF (10 mL) is cooled to 4° C. using an ice bath. An amine, tyramine (1 eq; 6.02 mmol) is added to the medium, followed by addition of a solution of BOP (benzotriazol-1-yloxy)tris(dimethylamino)phosphonium hexafluorophosphate (1 eq; 6.02 mmol) in dichloromethane (10 mL); the mixture is stirred for about thirty minutes in the ice bath and then for 20 hours at room temperature. Stirring is then stopped and the dichloromethane is evaporated off under vacuum. 100 mL of water are added to the remaining solution and the mixture obtained is extracted with ethyl acetate (3×75 mL). The organic phase is successively washed with 100 mL of 1N HCl solution, 100 mL of water and 100 mL of 1M sodium bicarbonate (NaHCO$_3$) solution. It is then dried over sodium sulfate and evaporated to dryness. The product is obtained in the form of a white precipitate after purification by chromatography on a column of silica gel.

Example 17

(Ester of para-coumaric acid):
2-(4-hydroxyphenyl)ethyl trans-coumarate

The protocol derived from Example 7 above is applied with p-coumaric acid and tyrosol instead of ferulic acid and tyrosol; the compound obtained is 2-(4-hydroxyphenyl)ethyl trans-coumarate (formula VIb, X and Y are CH)

Example 18

2-(4-hydroxyphenyl)ethyl dihydrocoumarate

The protocol derived from Example 7 above is applied with p-dihydrocoumaric acid (or phloretic acid) and tyrosol instead of ferulic acid and tyrosol; the compound obtained is 2-(4-hydroxyphenyl)ethyl dihydrocoumarate (formula VIb, X and Y are CH$_2$)

Example 19

N-3-(4-phosphatephenyl)propanoyl-2-(4-phosphatephenyl)ethylamine

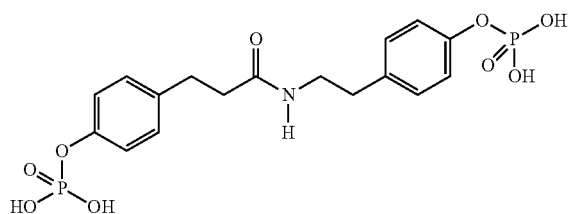 [SMILES: O=C(CCc1ccc(OP(=O)(O)O)cc1)NCCc1ccc(OP(=O)(O)O)cc1]

The product of Example 16 (180 mg; 0.63 mmol) and sodium hydride (37.8 mg; 1.57 mmol; 2.5 eq) are dispersed in 4 mL of anhydrous DMF (2 mL) under argon. The mixture obtained is stirred vigorously for 30 minutes at 0° C., and 1 mL of a solution of diethyl phosphate chloride (273 µL, 3 eq) in DMF (1 mL) is then added. Stirring is continued overnight. The reaction medium is poured into 10 mL of ice-water and extracted with ethyl acetate (2×10 mL). The organic phase is dried over sodium sulfate and evaporated to dryness to give a pale residue.

The residue obtained above (300 mg) is dissolved in 3 mL of anhydrous dichloromethane and the solution obtained is cooled to 0° C. An excess of trimethylsilyl bromide (1 mL) is added dropwise with stirring, and stirring is continued for 4 hours at room temperature. The solvent is then evaporated off under vacuum. The product is obtained in the form of a white precipitate after purification by reverse-phase chromatography in 85/15 water/methanol and freeze-drying of the column fractions.

Example 20

N-trans-3-(3-methoxy-4-phosphatephenyl)propenoyl-2-(4-phosphatephenyl)ethylamine The protocol of Example 19 is applied to the product derived from Example 1; the compound obtained is N-trans-3-(3-methoxy-4-phosphatephenyl)propenoyl-2-(4-phosphatephenyl)ethylamine.

Example 21

N-trans-3-(3,4-diphosphatephenyl)propenoyl-2-(4-phosphatephenyl)ethylamine

The protocol of Example 19 is applied to the product derived from Example 9; to the compound obtained is N-trans-3-(3,4-diphosphatephenyl)propenoyl-2-(4-phosphatephenyl)ethylamine

Example 22

N-trans-3-(3-methoxy-4-sulfatephenyl)propenoyl-2-(4-sulfatephenyl)ethylamine

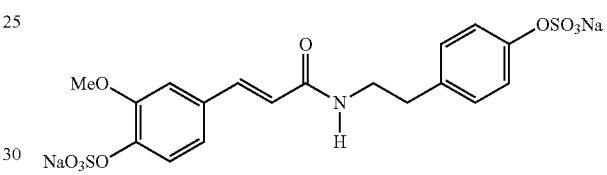

To a solution of the product derived from Example 3 (150 mg; 0.455 mmol) in 2 mL of DMF is added a complex of pyridine and of sulfur trioxide (2.73 mmol; 6 eq). The solution obtained is stirred for 20 hours at room temperature and 4 mL of aqueous sodium bicarbonate solution are then added. The product is obtained in the form of a white precipitate after purification by reverse-phase column chromatography (water).

Example 23

N-trans-3-(3-methoxy-4-sulfatephenyl)propenoyl-2-(3,4-disulfatephenyl)ethylamine The protocol of Example 22 is applied to the product derived from Example 1; the compound obtained is N-trans-3-(3-methoxy-4-sulfatephenyl)propenoyl-2(3,4-disulfatephenyl)ethylamine.

Example 24

N-3-4-sulfatephenyl)propanoyl-2-(4-sulfatephenyl) ethylamine

The protocol of Example 22 is applied to the product derived from Example 16; the compound obtained is N-3-(4-sulfatephenyl)propanoyl-2-(4-sulfatephenyl)ethylamine.

Example 25 of the Invention

The Invention Relates to Plant Extracts, Known to Contain One of the Para-Coumaric Acid Derivatives Described in the Above Examples As has been mentioned in the description, the present invention is advantageously performed using natural extracts, preferably plant extracts. Table 1 below describes the natural derivatives identified in plants.

TABLE 1

| Tyrosol derivatives | Formula | Plant | Family | Part |
| --- | --- | --- | --- | --- |
| p-Hydroxy-phenylethyl trans-p-coumarate | (structure) | *Stefania longa* *Polygonum orientale* | Menispermaceae Polygonaceae | Aerial parts Fruit |
| p-dihydro-coumaroyl-tyramine | (structure) | *Solanum tuberosum* | Solanaceae | Tuber (periderm) |
| teucrol | (structure) | *Teucrium pilosum* | Lamiaceae | Whole plant |
| p-Hydroxy-phenylethyl trans-ferulate | (structure) | *Stefania longa* *Polygonum orientale* *Coptidis* | Menispermaceae Polygonaceae Renonculaceae | Aerial parts Fruit Rhizome |
| N-trans-feruloyl-tyramine | (structure) | *Hibiscus cannabinus* *Piper* *Porcelia macrocarpa* | Malvaceae Piperaceae Annonaceae | Bark Fruit Branch |
| N-dihydro-feruloyl-tyramine | (structure) | *Annona cherimola* | Annonaceae | Stalk |
| N-trans-feruloyl-dopamine | (structure) | *Astraphaxis spinosa* | Polygonaceae | — |
| N-trans-caffeoyl-tyramine | (structure) | *Annona montana* *Limonium sinense* | Annonaceae Plumbaginaceae | Aerial parts Root |

TABLE 1-continued

| Tyrosol derivatives | Formula | Plant | Family | Part |
|---|---|---|---|---|
| N-dihydro-caffeoyl-tyramine | HO—⟨⟩—CH₂CH₂—C(O)—NH—CH₂CH₂—⟨⟩—OH (with HO- groups on left ring) | *Lycium chinense* | Solanaceae | Root |

Thus, various compositions were prepared from the plants of the above table. The invention covers any extract from these plants, in particular the extracts obtained according to Example 26 below.

It is thus preferred to perform an extraction preferably with a polar solvent or a mixture of polar solvents, optionally at reflux, preferably of the plant part mentioned in Table 1. Once the extraction has been performed, the solution is filtered and optionally redissolved in a polar solvent or a mixture of polar solvents.

Example 26 of the Invention

Extractions Performed using Plants known to Contain one of the para-coumaric Acid Derivatives Derived from the Invention Preferably, a *Hibiscus cannabinus* extract is prepared from chopped bark at 10% (w/w) in refluxing ethanol. The extraction is performed for 1 hour and the solution is then filtered, the ethanol is removed and the N-trans-feruloyltyramine (product derived from Example 3) obtained is dissolved to 5% (w/w) in a water/glycol mixture and then ultrafiltered through a ceramic filter with different cutoff thresholds, and finally filtered at 0.45 μm.

Preferably, a *Hibiscus cannabinus* extract is prepared from chopped bark at 10% (w/w) in ethyl acetate. The extraction is performed for 1 hour and the solution is then filtered, the ethyl acetate is removed and the N-trans-feruloyltyramine (product derived from Example 3) obtained is dissolved at 5% (w/w) in a water/glycol mixture and then ultrafiltered through a ceramic filter with different cutoff thresholds, and finally filtered at 0.45 μm.

Preferably, a *Hibiscus cannabinus* extract is prepared from chopped bark at 10% (w/w) in acetone. The extraction is performed for 1 hour and the solution is then filtered, the acetone is removed and the N-trans-feruloyltyramine (product derived from Example 3) obtained is dissolved at 5% (w/w) in a water/glycol mixture and then ultrafiltered through a ceramic filter with different cutoff thresholds, and finally filtered at 0.45 μm.

Preferably, an extract of *Hibiscus cannabinus* is prepared from chopped bark at 10% (w/w) in a mixture consisting of 75% water and 25% butylene glycol. The maceration is performed overnight at 45° C. and the N-trans-feruloyltyramine (product derived from Example 3) obtained is then ultrafiltered through a ceramic filter with different cutoff thresholds, and finally filtered at 0.45 μm.

Preferably, an extract of *Lycium chinense* is prepared from chopped roots at 10% (w/w) in refluxing ethanol. The extraction is performed for 1 hour and the solution is then filtered, the ethanol is removed and the N-trans-dihydrocaffeoyl-tyramine (product derived from Example 13) obtained is dissolved at 5% (w/w) in a water/glycol mixture and then ultrafiltered through a ceramic filter with different cutoff thresholds, and finally filtered at 0.45 μm.

Preferably, a *Lycium chinense* extract is prepared from chopped bark at 10% (w/w) in ethyl acetate. The extraction is performed for 1 hour and the solution is then filtered, the ethyl acetate is removed and the N-trans-dihydrocaffeoyltyramine (product derived from Example 13) obtained is dissolved at 5% (w/w) in a water/glycol mixture and then ultrafiltered through a ceramic filter with different cutoff thresholds, and finally filtered at 0.45 μm.

Preferably, a *Lycium chinense* extract is prepared from chopped bark at 10% (w/w) in acetone. The extraction is performed for 1 hour and the solution is then filtered, the acetone is removed and the N-trans-dihydrocaffeoyltyramine (product derived from Example 13) obtained is dissolved at 5% (w/w) in a water/glycol mixture and then ultrafiltered through a ceramic filter with different cutoff thresholds, and finally filtered at 0.45 μm.

An extract of *Lycium chinense* is prepared from chopped bark at 10% (w/w) in a mixture consisting of 75% water and 25% butylene glycol. The maceration is performed overnight at 45° C. and the N-trans-dihydrocaffeoyltyramine (product derived from Example 13) obtained is then ultrafiltered through a ceramic filter with different cutoff thresholds, and finally filtered at 0.45 μm.

The other extracts mentioned in Table 1 were also obtained according to the various protocols mentioned above with reference to the compounds of Examples 3 and 13. The protocol variations made are directly available to a person skilled in the art on the basis of his general knowledge.

Example 27 of the Invention

In Vitro Test of Inhibition of Isolated Tyrosinase with the p-coumaric Acid Derivatives Tyrosinase catalyses the formation of L-dopaquinone and then of dopachrome from L-dopa. Now, dopachrome is a coloured compound that may be quantified by visible spectrophotometry at 490 nm. The use of an active agent capable of modifying the enzymatic activity will be reflected by a variation in the optical density at 490 nm. The to ratio of the rates of formation of dopachrome makes it possible to determine precisely the activations or inhibitions obtained with the various test molecules.

The sample to be tested is incubated in the presence of fungal tyrosinase (Sigma), for 5 minutes with stirring. L-Dopa (Sigma), a tyrosinase substrate, is incubated for 10 minutes in the absence of light, in the presence or absence of the test molecules. The calculation of the percentage of inhibition is performed by relating the test OD to the OD of the negative control without molecule. The positive control used is kojic acid (Sigma) at 0.01%=45%±5% inhibition.

In the context of this in vitro test, the p-coumaric acid derivatives were tested at final concentrations of $10^{-4}$M and $10^{-5}$M. The results obtained are described in Table 2.

TABLE 2

Inhibition of fungal tyrosinase with various para-coumaric acid derivatives at 490 nm, expressed as a percentage of inhibition.

| Test derivatives | Mean $10^{-4}$M | Mean $10^{-5}$M | SD $10^{-4}$M | SD $10^{-5}$M |
|---|---|---|---|---|
| Example 11 | 12.03 | 3.7 | 2.99 | 2.09 |
| Example 9 | 27.42 | 13.06 | 0.24 | 1.24 |
| Example 10 | 16.23 | 14.72 | 1.83 | 0.87 |
| Example 12 | 17.32 | 20.26 | 1.06 | 1.19 |
| Example 3 | 29.41 | 10.16 | 1.33 | 5.37 |
| Example 4 | 1.35 | 0 | 1.26 | 1.02 |
| Example 1 | 9.18 | 0 | 1.65 | 0.59 |
| Example 2 | 0 | nd | 2.06 | nd |

SD: standard deviation
nd: not determined

It is clearly seen from Table 2 above that the test derivatives inhibit tyrosinase even at low concentrations.

Example 28 of the Invention

In Vitro Test of Inhibition of Human Tyrosinase with the p-Coumaric Acid Derivatives Human tyrosinase, obtained from melanocyte extracts obtained from healthy donors, catalyses the formation of L-dopaquinone from L-dopa. Now, the L-dopaquinone may be quantified by visible spectrophotometry at 490 nm by means of a chromogen: 3-methyl-2-benzothiazolinone hydrazone (MBTH). This reagent traps the o-quinones synthesized by tyrosinase to give a stable and soluble compound MBTH-o-quinone with a high molar optical density.

Thus, the use of an active agent capable of modifying the enzymatic activity will be reflected by a variation in the OD at 490 nm compared with that obtained in the negative control (100% activity).

The melanocyte extract is obtained after lysis of cell membranes of the normal human melanocytes, performed via a thermal shock. The supernatant is recovered and then incubated with MBTH (Sigma) and L-dopa (Sigma). The OD at 490 nm measured after 30 minutes is related, for each active agent tested, to that obtained for the control and the percentage of inhibition is calculated by relating the test OD (test molecule) to the OD for the negative control (without molecule). The positive control used is kojic acid at 0.1% (60%±5% inhibition). The results obtained are collated in Table 3.

TABLE 3

Inhibition of human tyrosinase with the p-coumaric acid derivatives at 490 nm, results expressed as percentage of inhibition.

| p-Coumaric acid derivatives | Mean $10^{-4}$M | Mean $10^{-5}$M | SD $10^{-4}$M | SD $10^{-5}$M |
|---|---|---|---|---|
| Example 11 | 0 | 8.68 | 3.29 | 1.74 |
| Example 9 | 22.09 | 11.88 | 5.46 | 3.04 |
| Example 10 | 9.91 | 11.45 | 2.53 | 3.28 |
| Example 12 | 6.53 | 0 | 1.88 | 0.69 |
| Example 3 | 0 | 7.56 | 5.87 | 3.43 |
| Example 4 | 6.42 | 4.92 | 0.95 | 2.52 |
| Example 1 | 0 | 0 | 4.22 | 5.87 |
| Example 2 | 0.94 | 0 | 1.92 | 4.22 |

It is seen from Table 3 above that the inhibitory activity of the para-coumaric acid derivatives is present but modest on this particular model of isolated human tyrosinase.

Example 29 of the Invention

Test of Inhibition of Human Tyrosinase Studied as a Monolayer after Application of the Test Active Agents to Normal Human Melanocytes Normal human melanocytes (obtained from abdominal surgery) are seeded in 24-well plates at a rate of 80 000 cells per well. They are cultured to confluence and the active agents are applied for 24 hours to the culture media. After 24 hours, the media are removed and the melanocytes are detached via mechanical action. An extraction is performed via a thermal shock and the supernatants are then recovered and incubated with MBTH (Sigma) and L-dopa (Sigma). The OD at 490 nm is measured after 30 minutes, and the tyrosinase inhibition is calculated by relating the OD at 490 nm to the protein content (measured in each culture well) of the test relative to the ratio: OD 490 nm/protein concentration of the negative control (untreated control). A percentage of anti-tyrosinase activity is thus calculated relative to the untreated control. The negative control of the experiment is kojic acid applied at 0.1% to the melanocytes (for a measured inhibition of 20%±5%).

TABLE 4

Inhibition of human tyrosinase after application of the p-coumaric acid derivatives and of the commercial products to normal human melanocytes, results expressed as percentage of inhibition (nd: not determined).

| Compounds | Mean $10^{-4}$M | Mean $10^{-5}$M | SD $10^{-4}$M | SD $10^{-5}$M |
|---|---|---|---|---|
| p-Dihydrocoumaric acid | 3.74 | nd | 1.62 | nd |
| p-Coumaric acid or p-hydroxycinnamic acid | 50.07 | nd | 4.67 | nd |
| Tyramine | 22.84 | nd | 3.21 | nd |
| Dopamine | 10.29 | | 2.4 | |
| Caffeic acid | 10.39 | 2.34 | 0.19 | 3.22 |
| Ferulic acid | 11.72 | 5.87 | 1.86 | 14.32 |
| Ferulic acid + dopamine (as a mixture) | 13.86 | nd | 1.2 | nd |
| Example 7 | 33.56 | 3.48 | 0.82 | 4.13 |
| Example 4 | 39.84 | 15.76 | 11.16 | 9.7 |
| Example 1 | 62.31 | 29.43 | 2.38 | 4.69 |
| Example 3 | 49.62 | 33.12 | 3.82 | 1.38 |
| Example 11 | nd | 28.03 | nd | 5.28 |
| Example 9 | 100 | 24.59 | 2.41 | 1.39 |
| Example 10 | 66.77 | 0 | 8.94 | 4.41 |
| Example 2 | 24.59 | 18.52 | 4.71 | 4.22 |
| Example 12 | nd | 5.63 | nd | 6.3 |
| Example 5 | 27.66 | nd | 7.17 | nd |
| Example 6 | 41.79 | nd | 5.19 | nd |
| Example 13 | 93.86 | 12.87 | 2.08 | 14.78 |
| Example 16 | 96.24 | 40.71 | 2.14 | 4.08 |

It is clearly seen from the above table that the results obtained in this model reflect real efficacy of the para-coumaric acid derivatives on the inhibition of human melanogenesis. The percentages of inhibition observed are markedly superior to those obtained on a model very remote from the human form, i.e. fungal tyrosinase, and by direct contact with a tyrosinase extracted from normal human melanocytes.

The hydroxylated para-coumaric acid derivatives thus show activity that is particularly unexpected to those skilled in the art and highly significant on the inhibition of hyman tyrosinase, whereas the efficacy is reduced on a less pertinent model using a fungal-based tyrosinase, which is widely used and described in the bibliography.

Tyramine and dopamine were tested at $10^{-4}$M (see above table) and showed very low activity. Molecules derived from the reaction between caffeic acid and tyramine or dopamine (the compounds derived from Examples 9 and 10, respectively) made it possible to very significantly increase the anti-tyrosinase activity, all the more so since caffeic acid alone also showed very low activity.

The molecules derived from the reaction between ferulic acid and tyramine or dopamine produce the same effect (the compounds derived from Examples 1 and 3, respectively), only ferulic acid also being very sparingly active.

The methyl analogue of dopamine makes it possible to obtain an inhibitory effect on melanin synthesis that is measurable but smaller than that of the non-methyl derivatives. The molecule derived from the reaction between caffeic acid and the methyl analogue of dopamine, on the one hand (compound derived from Example 12), and that derived from ferulic acid and from the same compound, on the other hand (compound derived from Example 2), do not allow such high activity.

Example 30 of the Invention

Test of Inhibition of Human Tyrosinase after Application of the Compounds Derived from Examples 9, 10, 1 and 3 to Normal Human Melanocytes Derived from Various Donors The compounds derived from the examples mentioned above were tested on melanocytes derived from various donors but of fair phototype, according to the protocol described in Example 29. The donors tested are as follows:

donor S (donor tested in Example 12): 46 years old donor 1: 40 years old donor 2: 47 years old donor 3: 33 years old The results obtained are described in the tables below:

TABLES 5

Inhibition of tyrosinase with the compounds of Examples 9, 10, 1 and 3 on 4 different donors.

|  | Mean $10^{-4}$ M | Mean $10^{-5}$ M | SD $10^{-4}$ M | SD $10^{-5}$ M |
|---|---|---|---|---|
| Example 9 |  |  |  |  |
| Donor S | 100 | 24.59 | 1.39 | 2.41 |
| Donor 1 | 65.33 | 0 | 5.25 | 28.87 |
| Donor 2 | 61.52 | 0 | 5.54 | 24.31 |
| Donor 3 | 70.68 | 22.21 | 2.1 | 8.68 |
| Example 10 |  |  |  |  |
| Donor S | 66.77 | 0 | 8.94 | 4.41 |
| Donor 1 | 44.6 | 0 | 5.76 | 9.43 |
| Donor 2 | 0 | 0.15 | 21.69 | 1.62 |
| Donor 3 | 14.38 | 3.32 | 6.64 | 11.24 |
| Example 1 |  |  |  |  |
| Donor S | 62.31 | 29.43 | 2.38 | 4.69 |
| Donor 1 | 63.89 | 35.79 | 4.42 | 4.54 |
| Donor 2 | 59.89 | 12.87 | 3.54 | 6.6 |
| Donor 3 | 50.17 | 18.93 | 7.72 | 2.5 |
| Example 3 |  |  |  |  |
| Donor S | 49.62 | 33.12 | 3.82 | 1.38 |
| Donor 1 | 44.81 | 0 | 8.55 | 35.85 |
| Donor 2 | 10.65 | 0 | 5.12 | 4.99 |
| Donor 3 | 57.89 | 42.45 | 7.52 | 8.9 |

The results obtained show great efficacy of the compounds on 4 different donors.

Example 31 of the Invention

Test of Inhibition of Human Tyrosinase after Application of the Compounds Derived from Examples 3, 9 and 1 to Normal Human Melanocytes Derived from Various Donors of Brown and Black Phototypes The compound derived from Example 1 is tested on cultures of melanocytes obtained from 2 donors of brown phototype and from one donor of black phototype. The protocol applied is that described in Example 29. The results obtained on the 2 donors to of brown phototype are described in Tables 6.

TABLES 6

Inhibition of tyrosinase obtained with the compound derived from Example 3 on 2 donors of brown phototype.

|  | Mean Donor A | Mean Donor B | SD Donor A | SD Donor B |
|---|---|---|---|---|
| Example 3 |  |  |  |  |
| $10^{-3}$ M | 85.57 | 87.4 | 8.36 | 3.15 |
| $10^{-4}$ M | 40.41 | 30.49 | 1.77 | 3.2 |
| $10^{-5}$ M | 15.55 | 16.71 | 2.03 | 6.87 |
| Example 9 |  |  |  |  |
| $10^{-3}$ M | 98.88 | 94.46 | 0.59 | 5.35 |
| $10^{-4}$ M | 44.59 | 44.4 | 11.49 | 1.59 |
| $10^{-5}$ M | 21.29 | 18.93 | 1.93 | 3.24 |
| Example 1 |  |  |  |  |
| $10^{-3}$ M | 99.38 | 87.23 | 0.13 | 6.01 |
| $10^{-4}$ M | 59.17 | 65.77 | 0.64 | 5.19 |
| $10^{-5}$ M | 29.27 | 20.78 | 2.59 | 6.14 |

The results obtained on the brown phototypes show that the anti-tyrosinase activity is dose-dependent and strong. The results obtained with the donor of black phototype (31 years old) are described in Table 7 below.

TABLE 7

Inhibition obtained for the compound derived from Examples 3 and 9 on a donor of negroid skin.

|  | Mean Negroid skin | SD |
|---|---|---|
| Example 3 |  |  |
| $10^{-4}$ M | 44.5 | 3.68 |
| $10^{-5}$ M | 21.95 | 4.76 |
| Example 9 |  |  |
| $10^{-4}$ M | 49.33 | 3.55 |
| $10^{-5}$ M | 16.01 | 1.15 |

The inhibitory activity on tyrosinase derived from the donor with negroid skin is dose-dependent and conforms the results obtained on the one hand on donors derived from fair phototypes.

Example 32 of the Invention

Study of the Cytotoxicity of Para-Coumaric Acid Derivatives

The cytotoxicity of the active agents is studied on normal human melanocytes in 24-well plates, via assay with PNPP (P-nitrophenyl phosphate), this substance being converted into p-nitrophenol via the intracellular acid phosphatases of viable cells. The absorbance of p-nitrophenol at 405 nm is directly proportional to the number of viable cells.

The active agents are tested at 2 different concentrations ($10^{-4}$ M and $10^{-5}$ M) and added to the culture medium and incubated at 37° C. for 24 hours. The assay with PNPP is performed on the cell lawn and the results are expressed as a percentage of viability relative to the negative control (untreated wells).

The results obtained are collated in Table 8 below:

TABLE 8

Percentages of viability obtained for the various p-coumaric acid derivatives on normal human melanocytes (the molecules were tested at 2 concentrations, $10^{-4}$ and $10^{-5}$ M.

|  | Mean $10^{-4}$ M | Mean $10^{-5}$ M | SD $10^{-4}$ M | SD $10^{-5}$ M |
|---|---|---|---|---|
| Example 3 | 102.55 | 111.54 | 0.296 | 0.081 |
| Example 4 | 101.94 | 99.55 | 0.095 | 0.191 |
| Example 9 | 77.9 | 94.96 | 0.101 | 0.147 |
| Example 10 | 84.62 | 102.1 | 0.09 | 0.045 |
| Example 11 | 39.02 | 116.99 | 0.039 | 0.09 |
| Example 12 | 33.51 | 109.84 | 0.053 | 0.111 |
| Example 1 | 94.49 | 119.83 | 0.082 | 0.083 |
| Example 2 | 114.29 | 114.6 | 0.043 | 0.085 |

The test molecules are non-cytotoxic when they are tested at molar concentrations of $10^{-4}$ and $10^{-5}$ M since the percentages of viability obtained are greater than 75% viability (tolerated threshold). Only 2 molecules have a threshold lower than 75% when tested at $10^{-4}$ M, i.e. the molecules derived from Examples 11 and 12. To be evaluated, these molecules will thus need to be tested as a monolayer at concentrations below $10^{-4}$ M (for example $10^{-5}$ M).

Example 33 of the Invention

Comparison of the Efficacy of the Para-Coumaric Acid Derivatives and of Quasi-Drug Molecules A study is performed with molecules known in the literature for their depigmenting activity; these molecules are applied to the model described in Example 29 so as to compare their efficacy relative to the molecules described in the various examples. Vitamin C stabilized with a magnesium phosphate group, or VitC MgP, and kojic acid were evaluated in our model. The results obtained are described in Table 9.

TABLE 9

Tyrosinase inhibition obtained for literature controls.

| Molecule and test concentration | Mean Inhibition (%) | SD | Cytotoxicity |
|---|---|---|---|
| VitC 3% | 97.77 | 1.15 | cell death |
| VitC 0.3% | 49.28 | 4.86 | cell death |
| VitC 0.03% | 0 | 7.3 | no |
| VitC MgP 3% | 0 | 1.65 | no |
| VitC MgP 0.3% | 1.55 | 3.28 | no |
| VitC MgP 0.03% | 2.93 | 2.79 | no |
| Kojic acid 0.5% | 25.09 | 3.2 | cell death |
| Kojic acid 0.05% | 14.26 | 4.37 | no |
| Kojic acid 0.005% | 6.84 | 4.32 | no |

The test molecules were found to be ineffective in the model described in Example 29 when compared with the para-coumaric acid derivatives, which are particularly active at much lower concentrations. Specifically, no molecule allowed human tyrosinase to be inhibited at a threshold comparable to that of the para-coumaric acid derivatives.

Vitamin C tested at 3% and 0.3% shows high levels of inhibition since this molecule has cytotoxic action on melanocytes and is non-specific. Consequently, this molecule cannot be considered as active in our model. The para-coumaric acid derivatives are found to be molecules that are highly effective on normal human tyrosinase.

Example 34 of the Invention

Study of the Antiradical Activity of the Para-Coumaric Acid Derivatives

The antiradical activity of the derivatives derived from the syntheses described above was evaluated in an in vitro acellular model using DPPH.

1,1-Diphenyl 2-picryihydrazyl, on account of its paramagnetic structure, can accept an electron or a hydrogen radical to become a stable diamagnetic molecule. This free radical, which is purple coloured in ethanol, has a strong absorption band at 520 nm.

The addition of a compound that provides electrons results in a decolorization of the 1,1-diphenyl 2-picrylhydrazyl that is proportional to the number of electrons taken up by the radical, which may be monitored by measuring the absorbance at 520 nm.

DPPH is incubated for 30 minutes in the presence of the derivatives described above, tested at a concentration of $10^{-5}$ M, or alone for the control. At the end of the incubation, the antiradical activity of the above derivatives is evaluated by measuring the absorbance of the solution at 520 nm.

The antiradical activity of each test product is calculated according to the formula, as a percentage:

$$100 - ((OD_{520} \text{ in the presence of the test compound}/OD_{520} \text{ in the absence of compound}) \times 100)$$

TABLE 10

Antiradical activity of the compounds derived from the invention:

| Compounds | Mean $10^{-5}$ M | SD $10^{-5}$ M |
|---|---|---|
| Example 4 | 15.72 | 2.86 |
| Example 1 | 60.01 | 8.03 |
| Example 3 | 13.73 | 2.03 |
| Example 11 | 59.2 | 2.54 |
| Example 9 | 41.17 | 2.60 |
| Example 10 | 57.45 | 2.39 |
| Example 2 | 20.16 | 0.96 |
| Example 12 | 44.51 | 3.45 |

The compounds described above show antiradical activity, at a concentration of $10^{-5}$ M. On account of their high antiradical activity, the compounds derived from the invention are antiinflammatory compounds: specifically, the free radicals generated during a UV stress or the like induce the inflammation cascade. This is why compounds with antiradical properties inhibit the inflammation cascade.

The term "products of the invention" means the compounds corresponding to the general formula I, and also the preferred compounds and especially the compounds described in Examples 1 to 26.

Example 35 of the invention

Use of the Products of the Invention in Cosmetic or Pharmaceutical Formulations of Oil-in-Water Emulsion Type Formulation 35a:

| A | Water | qs 100 |
|---|---|---|
|   | Butylene Glycol | 2 |
|   | Glycerol | 3 |
|   | Sodium Dihydroxycetyl Phosphate, Isopropyl Hydroxycetyl Ether | 2 |
| B | Glycol Stearate SE | 14 |
|   | Triisononaoin | 5 |
|   | Octyl Cocoate | 6 |
| C | Butylene Glycol, Methylparaben, Ethylparaben, Propylparaben, pH adjusted to 5.5 | 2 |
| D | Products of the invention | 0.01-10% |

Formulation 35b:

| A | Water | qs 100 |
|---|---|---|
|   | Butylene Glycol | 2 |
|   | Glycerol | 3 |
|   | Polyacrylamide, Isoparaffin, Laureth-7 | 2.8 |
| B | Butylene Glycol, Methylparaben, Ethylparaben, Propylparaben; | 2 |
|   | Phenoxyethanol, Methylparaben, Propylparaben, Butylparaben, Ethylparaben | 2 |
|   | Butylene Glycol | 0.5 |
| D | Products of the invention | 0.01-10% |

Formulation 35c:

| A | Carbomer | 0.50 |
|---|---|---|
|   | Propylene Glycol | 3 |
|   | Glycerol | 5 |
|   | Water | qs 100 |
| B | Octyl Cocoate | 5 |
|   | Bisabolol | 0.30 |
|   | Dimethicone | 0.30 |
| C | Sodium Hydroxide | 1.60 |
| D | Phenoxyethanol, Methylparaben, Propylparaben, Butylparaben, Ethylparaben | 0.50 |
| E | Fragrance | 0.30 |
| F | Products of the invention | 0.01-10% |

Example 36 of the Invention

Use of the Products of the Invention in a Formulation of Water-in-Oil Type

| A | PEG 30-dipolyhydroxystearate | 3 |
|---|---|---|
|   | Capric Triglycerides | 3 |
|   | Cetearyl Octanoate | 4 |
|   | Dibutyl Adipate | 3 |
|   | Grape Seed Oil | 1.5 |
|   | Jojoba Oil | 1.5 |
|   | Phenoxyethanol, Methylparaben, Propylparaben, Butylparaben, Ethylparaben | 0.5 |
| B | Glycerol | 3 |
|   | Butylene Glycol | 3 |
|   | Magnesium Sulfate | 0.5 |
|   | EDTA | 0.05 |
|   | Water | qs 100 |
| C | Cyclomethicone | 1 |
|   | Dimethicone | 1 |
| D | Fragrance | 0.3 |
| E | Products of the invention | 0.01-10% |

Example 37 of the Invention

Use of the Products of the Invention in a Formulation of Shampoo or Shower Gel Type

| A | Xantham Gum | 0.8 |
|---|---|---|
|   | Water | qs 100 |
| B | Butylene Glycol, Methylparaben, Ethylparaben, Propylparaben | 0.5 |
|   | Phenoxyethanol, Methylparaben, Propylparaben, Butylparaben, Ethylparaben | 0.5 |
| C | Citric acid | 0.8 |
| D | Sodium Laureth Sulfate | 40.0 |
| E | Produit of the invention | 0.01-10% |

Example 38 of the Invention

Use of the Products of the Invention in a Formulation of Lipstick Type and Other Anhydrous Products

| A | Mineral Wax | 17.0 |
|---|---|---|
|   | Isostearyl Isostearate | 31.5 |
|   | Propylene Glycol Dipelargonate | 2.6 |
|   | Propylene Glycol Isostearate | 1.7 |
|   | PEG 8 Beeswax | 3.0 |
|   | Hydrogenated Palm Kernel Oil Glycerides, Hydrogenated Palm Glycerides | 3.4 |
|   | Lanolin Oil | 3.4 |
|   | Sesame Oil | 1.7 |
|   | Cetyl Lactate | 1.7 |
|   | Mineral Oil, Lanolin Alcohol | 3.0 |
| B | Castor Oil | qs 100 |
|   | Titanium Dioxide | 3.9 |
|   | CI 15850: 1 | 0.616 |
|   | CI 45410: 1 | 0.256 |
|   | CI 19140: 1 | 0.048 |
|   | CI 77491 | 2.048 |
| C | Products of the invention | 0.01-5% |

Example 39 of the Invention

Use of the Products of the Invention in an Aqueous Gel Formulation (Eye Contours, Slimming, Etc.)

| A | Water | qs 100 |
|---|---|---|
|   | Carbomer | 0.5 |
|   | Butylene Glycol | 15 |
|   | Phenoxyethanol, Methylparaben, Propylparaben, Butylparaben, Ethylparaben | 0.5 |
| B | Products of the invention | 0.01-10% |

Example 40 of the Invention

Use of the Products of the Invention in a Formulation of Triple Emulsion Type

Primary emulsion W1/O

| A | PEG 30-dipolyhydroxystearate | 4 |
|---|---|---|
|   | Capric Triglycerides | 7.5 |
|   | Isohexadecane | 15 |
|   | PPG-15 Stearyl ether | 7.5 |
| B | Water | 65.3 |
| C | Phenoxyethanol, Methylparaben, Propylparaben, Butylparaben, Ethylparaben | 0.7 |

Secondary emulsion W1/O/W2

| A | Primary emulsion | 60 |
|---|---|---|
| B | Poloxamer 407 | 2 |
|   | Phenoxyethanol, Methylparaben, Propylparaben, 2-bromo-2-nitropropane-1,3-diol | 0.3 |
|   | Water | qs 100 |
| C | Carbomer | 15 |
| D | Triethanolamine | pH 6.0-6.5 |

Example 41 of the Invention

Preparation of Pharmaceutical Formulations Containing the Product of the Invention Formulation 41a: Preparation of Tablets

| A | Excipients | In g per tablet |
|---|---|---|
|   | Lactose | 0.359 |
|   | Sucrose | 0.240 |
| B | Products of the invention* | 0.001-0.1 |

*The product of the invention is obtained, for example, according to the extraction process described in Example 1 followed by a drying step.

Formulation 41b: Preparation of a Pomade

| A | Excipients | |
|---|---|---|
|   | Low-density polyethylene | 5.5 |
|   | Liquid paraffin | qs 100 |
| B | Products of the invention* | 0.001-0.1 |

*The product of the invention is obtained, for example, according to the extraction process described in Example 1 followed by a drying step.

Formulation 41c: Preparation of an Injectable Formula

| A | Excipient | |
|---|---|---|
|   | Isotonic saline solution | 5 ml |
| B | Products of the invention* | 0.001-0.1 g |

*The product of the invention is obtained, for example, according to the extraction process described in Example 1 followed by a drying step.

Example 42

Evaluation of the Cosmetic Acceptance of a Preparation Containing the Product of the Invention The toxicology tests were performed on the compound obtained according to Example 1 incorporated at 10% into a 0.5% xanthan gel, by ocular evaluation on rabbits, by studying the absence of abnormal toxicity via single oral administration to rats, and by studying the sensitizing power on guinea pigs.

Evaluation of the Primary Skin Irritation in Rabbits:

The preparations described above are applied without dilution at a dose of 0.5 ml to the skin of 3 rabbits according to the method recommended by the OCDE Directive concerning the study of "the acute irritant/corrosive effect on the skin". The products are classified according to the criteria defined by the decree of 1/2/1982 published in the JORF of 21/02/82. The results of these tests made it possible to conclude that the products of the invention were classified as non-irritant to the skin.

Evaluation of the Ocular Irritation in Rabbits:

The preparations described above were instilled pure, in a single application, at a rate of 0.1 ml, into the eye of 3 rabbits according to the method recommenced by the OCDE Directive No. 405 of 24 February 1987 concerning the study of the "acute irritant/corrosive effect on the eyes". The results of this test make it possible to conclude that the preparations may be considered as non-irritant to the eyes, within the meaning of the Directive 91/326 EC, used pure or without dilution.

Test on the Absence of Abnormal Toxicity Via Single Oral Administration to Rats:

The preparations described were administered in a single portion orally at a dose of 2 g/kg of body weight, to 5 male rats and 5 female rats according to a protocol inspired by the OCDE Directive No. 401 of 24 February 1987 and adapted to cosmetic products. The $LD_0$ and $LD_{50}$ are found to be greater than 2000 mg/kg. The preparations tested are therefore not classified among the preparations hazardous by ingestion.

Evaluation of the Skin Sensitization Potential in Guinea Pigs:

The preparations described are subjected to the maximization test described by Magnusson and Kligmann, which protocol is in accordance with the OCDE guideline No. 406. The preparations are classified as not sensitizing on contact with the skin.

TABLE 11

CHEMICAL FORMULAE

| Products | Structural formulae |
|---|---|
| Tyramine hydrochloride | 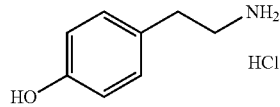 |
| 3-Hydroxytyramine Hydrochloride (Dopamine Hydrochloride) | 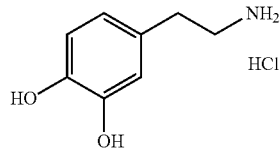 [SMILES: NCCc1ccc(O)c(O)c1 ; Cl] |

| Examples | Formulae |
|---|---|
| Example 3 (N-trans-Feruloyltyramine) | 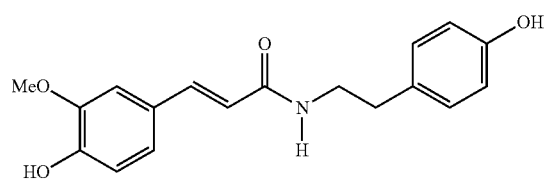 [SMILES: COc1cc(/C=C/C(=O)NCCc2ccc(O)cc2)ccc1O] |
| Example 4 (N-trans-Feruloyl-4-hydroxy-3-methoxyphenylmethylamine) | 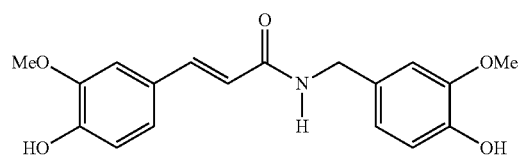 [SMILES: COc1cc(/C=C/C(=O)NCc2ccc(O)c(OC)c2)ccc1O] |
| Example 9 (N-trans-Caffeoyltyramine) | 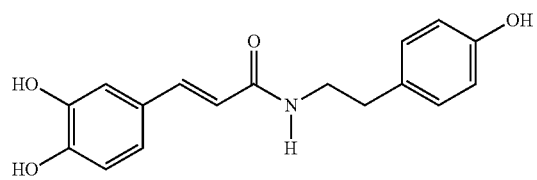 [SMILES: O=C(/C=C/c1ccc(O)c(O)c1)NCCc1ccc(O)cc1] |
| Example 10 (N-trans-Caffeoyldopamine) | 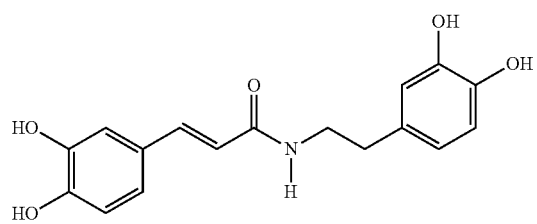 [SMILES: O=C(/C=C/c1ccc(O)c(O)c1)NCCc1ccc(O)c(O)c1] |
| Example 11 (N-trans-Caffeoyl-4-hydroxy-3-methoxyphenylmethylamine) | 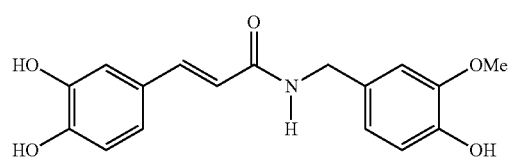 [SMILES: COc1cc(CNC(=O)/C=C/c2ccc(O)c(O)c2)ccc1O] |
| Example 12 (N-trans-Caffeoyl-3,4-dimethoxydopamine) | 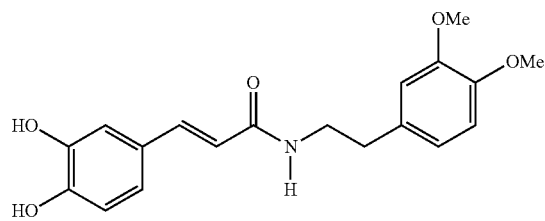 [SMILES: COc1ccc(CCNC(=O)/C=C/c2ccc(O)c(O)c2)cc1OC] |

TABLE 11-continued
CHEMICAL FORMULAE
Example 1 (N-trans-Feruloyldopamine)
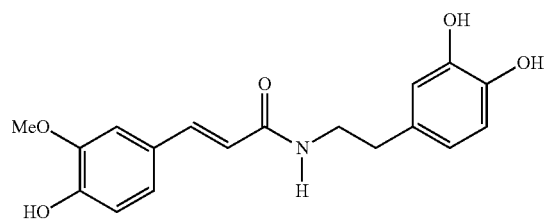 [SMILES: COc1cc(/C=C/C(=O)NCCc2ccc(O)c(O)c2)ccc1O]
Example 2 (N-trans-Feruloyl-3,4-dimethoxydopamine)
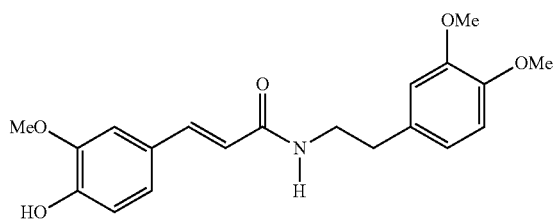 [SMILES: COc1cc(/C=C/C(=O)NCCc2ccc(OC)c(OC)c2)ccc1O]
Example 5 (N-Dihydroferuloyltyramine)
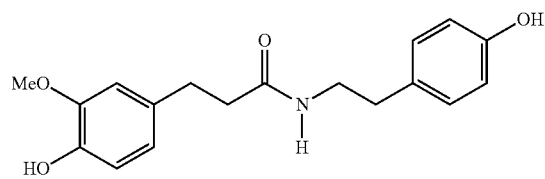 [SMILES: COc1cc(CCC(=O)NCCc2ccc(O)cc2)ccc1O]
Example 6 (N-Dihydroferuloyldopamine)
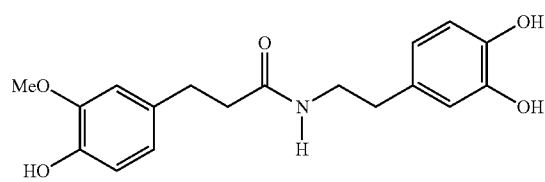 [SMILES: COc1cc(CCC(=O)NCCc2ccc(O)c(O)c2)ccc1O]
Example 16 (3-(4-Hydroxyphenyl)-N-(2-[4-hydroxyphenyl]ethyl)propanamide)
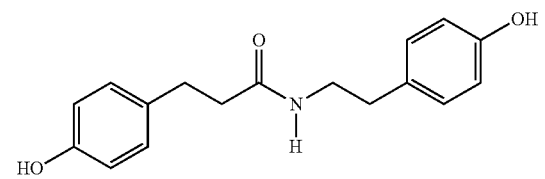 [SMILES: O=C(CCc1ccc(O)cc1)NCCc1ccc(O)cc1]
Example 13 (Dihydrocaffeoyltyramine)
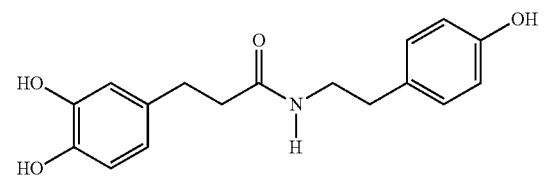 [SMILES: O=C(CCc1ccc(O)c(O)c1)NCCc1ccc(O)cc1]
Example 19 N-3-(4-Phosphatephenyl)-propanoyl-2-(4-phosphatephenyl)-ethylamine
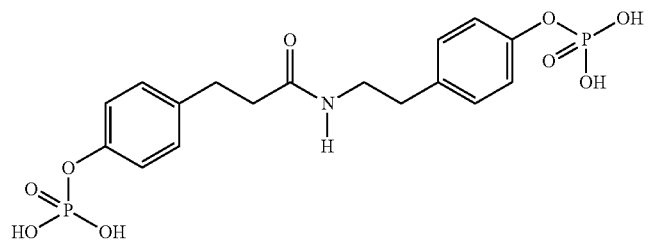 [SMILES: O=C(CCc1ccc(OP(=O)(O)O)cc1)NCCc1ccc(OP(=O)(O)O)cc1]

TABLE 11-continued

| CHEMICAL FORMULAE | |
|---|---|
| Example 20 N-trans-3-(3-Methoxy-4-phosphatephenyl)propenoyl-2-(4-phosphatephenyl)ethylamine | 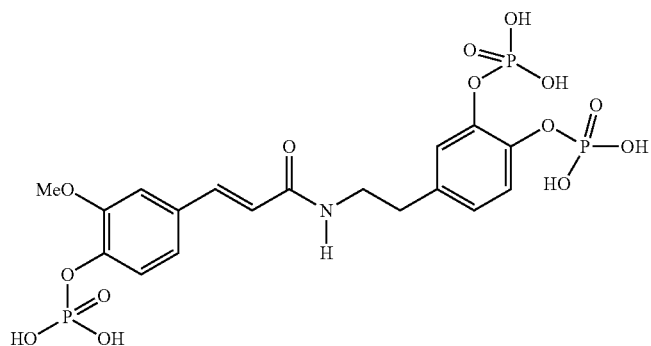 [SMILES: COc1cc(/C=C/C(=O)NCCc2ccc(OP(=O)(O)O)c(OP(=O)(O)O)c2)ccc1OP(=O)(O)O] |
| Example 21 N-trans-3-(3,4-Diphosphatephenyl)propenoyl-2-(4-phosphatephenyl)ethylamine | 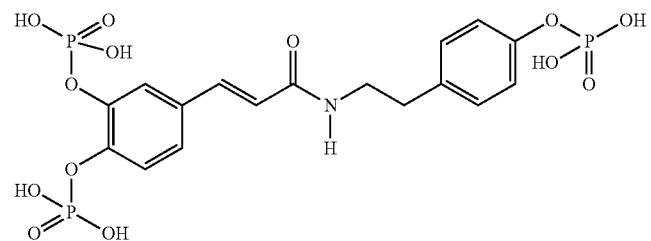 [SMILES: O=C(/C=C/c1ccc(OP(=O)(O)O)c(OP(=O)(O)O)c1)NCCc1ccc(OP(=O)(O)O)cc1] |

| Example | Formulae |
|---|---|
| Example 22 N-trans-3-(3-Methoxy-4-sulfatephenyl)propenoyl-2(4-sulfatephenyl)ethylamine | 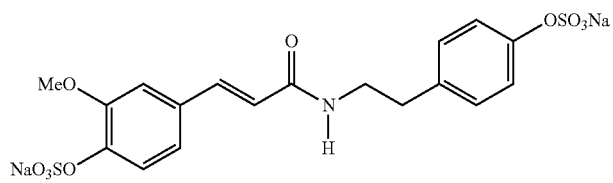 |
| Example 23 N-trans-3-(3-Methoxy-4-sulfatephenyl)propenoyl-2(3,4-disulfatephenyl)ethylamine | 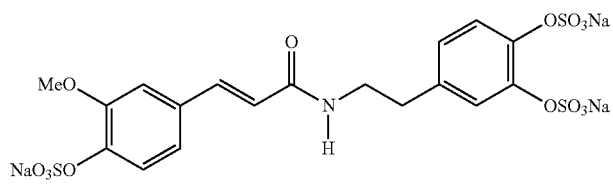 |
| Example 24 N-3-(4-Sulfatephenyl)-propanoyl-2-(4-sulfatephenyl)ethylamine | 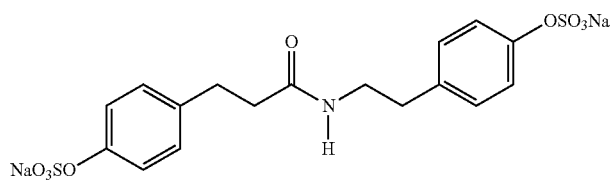 |

| Examples | Formulae |
|---|---|
| Example 7 2-(p-Hydroxyphenylethyl) trans-ferulate | 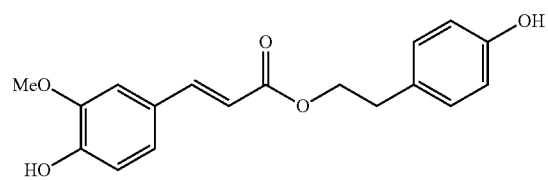 [SMILES: COc1cc(/C=C/C(=O)OCCc2ccc(O)cc2)ccc1O] |

TABLE 11-continued

CHEMICAL FORMULAE

Example 8
2-(3,4-Dihydroxyphenylethyl) trans-ferulate

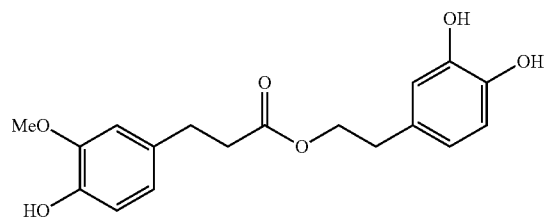 [SMILES: COc1cc(CCC(=O)OCCc2ccc(O)c(O)c2)ccc1O]

Example 14
2-(4-Hydroxyphenyl)ethyl trans-caffeoate

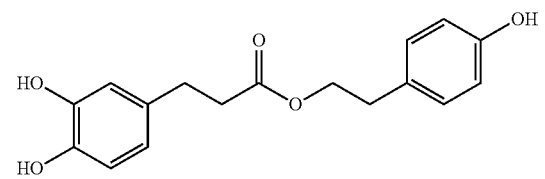 [SMILES: O=C(CCc1ccc(O)c(O)c1)OCCc1ccc(O)cc1]

Example 15
2-(3,4-Dihydroxyphenyl)ethyl trans-caffeoate

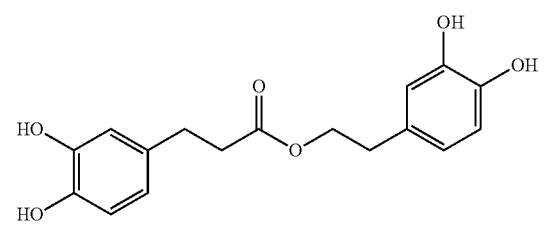 [SMILES: O=C(CCc1ccc(O)c(O)c1)OCCc1ccc(O)c(O)c1]

Example 17
2-(4-Hydroxyphenyl)ethyl trans-coumarate

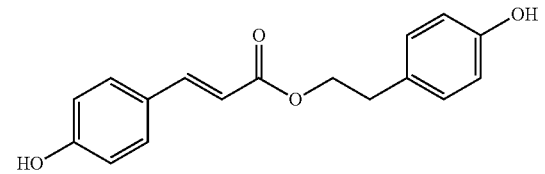 [SMILES: O=C(/C=C/c1ccc(O)cc1)OCCc1ccc(O)cc1]

Example 18
2-(4-Hydroxyphenyl)ethyl dihydrocoumarate

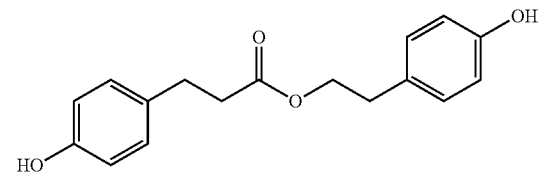 [SMILES: O=C(CCc1ccc(O)cc1)OCCc1ccc(O)cc1]

The invention claimed is:

1. A method of reducing skin pigmentation, comprising applying to an area of human skin in need of reduced pigmentation a topical composition comprising an amount of a compound of formula (III)

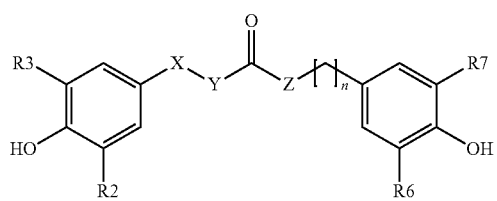

effective to reduce skin pigmentation,
wherein Z represents an oxygen or an —NH— group;
X and Y are identical and each represent a CH group (cis or trans) or $CH_2$ group;
n is a number, preferably an integer, ranging from 1 to 12;
$R_2$, $R_3$, $R_6$ and $R_7$ are, independently of each other: a hydrogen atom; a hydroxyl group; a halogen atom; a salified or non-salified acid function; an aldehyde function; an amide function; a primary, secondary, or tertiary amine function in basic or salified form; a cyano group; a thiol group; a nitro group; a sugar; an O-heteroside; a linear or branched alkoxide group; a linear or branched alkyl chain; a linear or branched alkenyl chain; a linear or branched thioalkyl chain; a linear or branched alkoxy chain; an alkenyloxy chain; a salified or non-salified sulfate group; a salified or non-salified sulfonyl group; a salified or non-salified phosphonate group; a salified or non-salified phosphate group; or a silanol group in which one or more carbon-based chains may be substituted.

2. The method of claim 1 wherein the compound has the formula (III) in which n=2.

3. The method of claim 2 wherein the compound has the following formula (IVa)

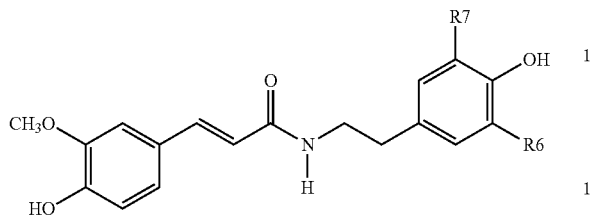

IVa wherein R$_6$ and R$_7$ are as defined in claim 1.

4. The method of claim 3, wherein R$_6$ is a hydroxyl group and R$_7$ is a hydrogen atom.

5. The method of claim 1, wherein the compound is extracted from a plant.

6. The method of claim 1, wherein the topical composition further comprises at least one topically acceptable excipient.

7. The method of claim 1, wherein the topical composition is a cosmetic composition.

8. The method of claim 7, wherein the cosmetic composition further comprises at least one other cosmetically active ingredient.

9. The method of claim 1, wherein the topical composition is a pharmaceutical composition for the treatment of hyperpigmentation.

10. A method of cosmetic care, comprising topically applying a cosmetic composition to at least one area of the skin tissue of an individual having hyperpigmentation, wherein the cosmetic composition comprises an amount of a compound of formula (III)

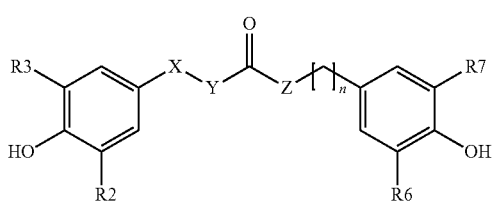

III effective to reduce skin pigmentation in the area of application, wherein Z represents an oxygen or an —NH— group;

X and Y are identical and each represent a CH group (cis or trans) or CH$_2$ group;

n is a number, preferably an integer, ranging from 1 to 12;

R$_2$, R$_3$, R$_6$ and R$_7$ are, independently of each other: a hydrogen atom; a hydroxyl group; a halogen atom; a salified or non-salified acid function; an aldehyde function; an amide function; a primary, secondary, or tertiary amine function in basic or salified form; a cyano group; a thiol group; a nitro group; a sugar; an O-heteroside; a linear or branched alkoxide group; a linear or branched alkyl chain; a linear or branched alkenyl chain; a linear or branched thioalkyl chain; a linear or branched alkoxy chain; an alkenyloxy chain; a salified or non-salified sulfate group; a salified or non-salified sulfonyl group; a salified or non-salified phosphonate group; a salified or non-salified phosphate group; or a silanol group in which one or more carbon-based chains may be substituted.

11. The method of claim 10 wherein the compound has the formula (III) in which n=2.

12. The method of claim 11 wherein the compound has the following formula (IVa)

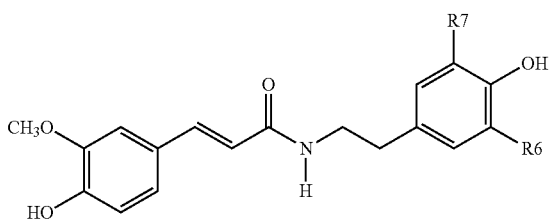

IVa wherein R$_6$ and R$_7$ are as defined in claim 1.

13. The method of claim 12, wherein R$_6$ is a hydroxyl group and R$_7$ is a hydrogen atom.

14. The method of claim 10, wherein the compound is extracted from a plant.

15. The method of claim 10, wherein the cosmetic composition further comprises at least one other cosmetically active ingredient.

16. The method of claim 10, wherein the cosmetic composition further comprises at least one topically acceptable excipient.

17. A method of melanogenesis inhibition comprising topically applying to at least one area of skin tissue in need of melanogenesis inhibition a composition comprising an amount of a compound of formula (III)

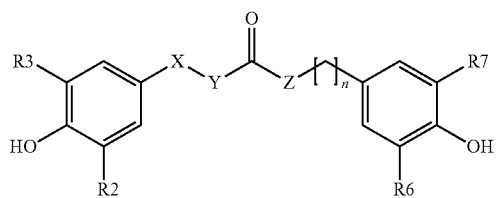

III effective to inhibit melanogenesis, wherein Z represents an oxygen or an —NH— group;

X and Y are identical and each represent a CH group (cis or trans) or CH$_2$ group;

n is a number, preferably an integer, ranging from 1 to 12;

R$_2$, R$_3$, R$_6$ and R$_7$ are, independently of each other: a hydrogen atom; a hydroxyl group; a halogen atom; a salified or non-salified acid function; an aldehyde function; an amide function; a primary, secondary, or tertiary amine function in basic or salified form; a cyano group; a thiol group; a nitro group; a sugar; an O-heteroside; a linear or branched alkoxide group; a linear or branched alkyl chain; a linear or branched alkenyl chain; a linear or branched thioalkyl chain; a linear or branched alkoxy chain; an alkenyloxy chain; a salified or non-salified sulfate group; a salified or non-salified sulfonyl group; a salified or non-salified phosphonate group; a salified or non-salified phosphate group; or a silanol group in which one or more carbon-based chains may be substituted.

18. The method of claim 17 wherein the compound has the formula (III) in which n=2.

19. The method of claim 18 wherein the compound has the following formula (IVa)

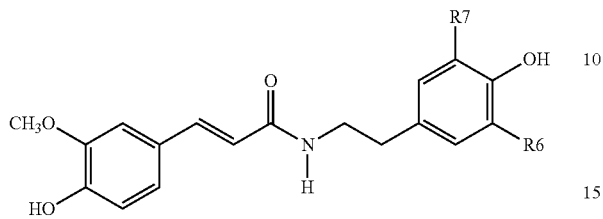

IVa wherein $R_6$ and $R_7$ are as defined in claim 1.

20. The method of claim 19, wherein $R_6$ is a hydroxyl group and $R_7$ is a hydrogen atom.

21. The method of claim 17, wherein the compound is extracted from a plant.

22. The method of claim 17, wherein the composition is a cosmetic composition.

23. The method of claim 22, wherein the cosmetic composition further comprises at least one other cosmetically active ingredient.

24. The method of claim 17, wherein the composition further comprises at least one topically acceptable excipient.

25. The method of claim 17, wherein the composition is a pharmaceutical composition for the treatment of hyperpigmentation.

* * * * *